US009925246B2

(12) United States Patent
Basile et al.

(10) Patent No.: US 9,925,246 B2
(45) Date of Patent: Mar. 27, 2018

(54) MITIGATION OF CUTANEOUS INJURY WITH IL-12

(75) Inventors: Lena A. Basile, Tujunga, CA (US); Dolph Ellefson, Blue Jay, CA (US); Timothy K. Gallaher, Arcadia, CA (US)

(73) Assignee: NEUMEDICINES, INC., Pasadena, CA (US)

( * ) Notice: Subject to any disclaimer, the term of this patent is extended or adjusted under 35 U.S.C. 154(b) by 225 days.

(21) Appl. No.: 14/125,887

(22) PCT Filed: Jun. 13, 2012

(86) PCT No.: PCT/US2012/042165
§ 371 (c)(1),
(2), (4) Date: Mar. 17, 2014

(87) PCT Pub. No.: WO2012/174056
PCT Pub. Date: Dec. 20, 2012

(65) Prior Publication Data
US 2014/0205561 A1      Jul. 24, 2014

Related U.S. Application Data

(60) Provisional application No. 61/496,472, filed on Jun. 13, 2011, provisional application No. 61/528,053, filed on Aug. 26, 2011.

(51) Int. Cl.
*A61K 38/20* (2006.01)
*A61K 9/00* (2006.01)

(52) U.S. Cl.
CPC .......... *A61K 38/208* (2013.01); *A61K 9/0014* (2013.01); *A61K 9/0019* (2013.01)

(58) Field of Classification Search
CPC ... A61K 38/208; A61K 9/0019; A38K 9/0014
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,648,467 A | 7/1997 | Trinchieri et al. | |
| 5,744,132 A | 4/1998 | Warne et al. | |
| 5,756,085 A | 5/1998 | Sykes et al. | |
| 5,853,714 A | 12/1998 | Deetz et al. | |
| 6,423,308 B1* | 7/2002 | Yarchoan et al. | 424/85.2 |
| 6,683,046 B1 | 1/2004 | Gately et al. | |
| 7,052,685 B1 | 5/2006 | Rook | |
| 7,575,741 B2 | 8/2009 | Bowman et al. | |
| 2005/0136034 A1* | 6/2005 | Chen et al. | 424/85.2 |
| 2006/0039892 A1 | 2/2006 | Dede et al. | |
| 2008/0167239 A1 | 7/2008 | Rosen et al. | |
| 2008/0228456 A1 | 9/2008 | Clermont et al. | |
| 2010/0221208 A1 | 9/2010 | Gomer et al. | |
| 2010/0330046 A1* | 12/2010 | Comer | A61K 38/208 424/93.7 |
| 2011/0135597 A1 | 6/2011 | Bowman et al. | |

FOREIGN PATENT DOCUMENTS

| | | | |
|---|---|---|---|
| WO | WO 2005/007093 A2 | 1/2005 | |
| WO | WO 2010/135655 A2 | 11/2010 | |

OTHER PUBLICATIONS

DiPietro, L.A. et al. MIP-1alpha as a critical macrophage chemoattractant in murine wound repair. Journal of Clinical Investigation, 1998, vol. 101, No. 8, p. 1693-1698.*
Schwarz, A. et al. Interleukin-12 suppresses ultraviolet radiation-induced apoptosiss by inducing DNA repair. Nature Cell Biology, 2002, vol. 4, p. 26-31.*
Watford, W.T. et al. Signaling by IL-12 and IL-23 and the immunoregulatory roles of STAT4. Immunological Reviews, 2004, vol. 202, p. 139-156.*
Cummings, R. J. et al. Migration of skin dendritic cells in response to ionizing radiation expousre. Radiation Research, 2009, vol. 171(6), p. 687-697.*
International Search Report issued in related International Patent Application No. PCT/US2012/042165, completed Jul. 31, 2012.
Written Opinion issued in related International Patent Application No. PCT/U52012/042165, dated Aug. 17, 2012.
Al-Waili et al., Effects of Hyperbaric Oxygen on Inflammatory Response to Wound and Trauma: Possible Mechanism of Action, *The Scientific World Journal*, vol. 6, pp. 425-441 (2006).
Barrie et al., The Interleukin-12 Family of Cytokines: Therapeutic Targets for Inflammatory Disease Mediation, *Clinical and Applied Immunology Reviews*, No. 5, pp. 225-240 (2005).
Airoldi et al., Expression and Function of IL-12 and IL-18 Receptors on Human Tonsillar B Cells, 2000, Journal of Immunology., 165:6880-6888.
Brunda et al., Antitumor and antimetastatic activity of interleukin 12 against murine tumors, 1993, J. Exp. Med., 178:1223-1230.
Colombo, M. et al. "Interleukin-12 in Anti-tumor Immunity and Immunotherapy." Cytokine & Growth *Factor Reviews*, vol. 13, 155-168 (2002).
Cui et al., Requirement for Valpha14 NKT cells in IL-12-mediated rejection of tumors, 1997, Science, 278:1623-1626.
Dalod et al., Interferon alpha/beta and interleukin 12 responses to viral infections: pathways regulating dendritic cell cytokine expression in vivo, 2002, J. Exp. Med., 195:517-528.
Freireich, E.J. et al., "Quantitative Comparison of Toxicity of Anticancer Agents in Mouse, Rat, Hamster, Dog, Monkey, and Man." Cancer Chemotherapy Reports, vol. 50, pp. 219- (1966).

(Continued)

Primary Examiner — Robert S Landsman
Assistant Examiner — Bruce D. Hissong
(74) Attorney, Agent, or Firm — Foley & Lardner LLP

(57) ABSTRACT

The present application relates to treatment of cutaneous wounds using IL-12. The methods of the invention result in improved wound closure. The methods comprise treating cutaneous wounds using topical, subcutaneous, and/or intramuscular administration of IL-12.

29 Claims, 14 Drawing Sheets

(56) References Cited

OTHER PUBLICATIONS

Hirao et al., Synergism of interleukin 12, interleukin 3 and serum factor on primitive human hematopoietic progenitor cells, 1995, Stem Cells, 13:47-53.
Hsieh et al., Development of TH1 CD4+ T cells through IL-12 produced by Listeria-induced macrophages, 1993, Science, 260:547-549.
Jacobsen et al., Cytotoxic lymphocyte maturation factor (interleukin 12) is a synergistic growth factor for hematopoietic stem cells, *J. Exp Med.*, 178(2), pp. 413-418 (1993).
Lertmemongkolchai et al., Bystander activation of CD8+ T cells contributes to the rapid production of IFN-gamma in response to bacterial pathogens, *Journal of Immunology.*, 166:1097-1105 (2001).
Manetti et al., Natural killer cell stimulatory factor (interleukin 12 [IL-12]) induces T helper type 1 (Th1)-specific immune responses and inhibits the development of IL-4-producing Th cells, J. Exp. Med., vol. 177, pp. 1199-1204 (1993).
Noguchi et al., Effect of interleukin 12 on tumor induction by 3-methylcholanthrene, 1996, PNAS, 93:11798-11801.
Ohteki et al., Interleukin 12-dependent interferon gamma production by CD8alpha+ lymphoid dendritic cells, 1999, J. Exp. Med., 189:1981-1986.
Ploemacher, R., et al. "Interleukin-12 Enhances Interleukin-3 Dependent Multilineage Hematopoietic Colony Formation Stimulated by Interleukin-11 or Steel Factor." *Leukemia*, vol. 7, No. 9, pp. 1374-1380 (1993).
Presky et al., A functional interleukin 12 receptor complex is composed of two beta-type cytokine receptor subunits., 1996, PNAS, 93:14002-14007.
Reis de Sousa et al, In vivo microbial stimulation induces rapid CD40 ligand-independent production of interleukin 12 by dendritic cells and their redistribution to T cell areas, 1997, J. Exp. Med., 186:1819-1829.
Wu et al., "Biological function and distribution of human interleukin-12 receptor βchain," *Eur. J. Immunol.*, vol. 26, pp. 345-350 (1996).
Yao et al., Effective targeting of tumor vasculature by the angiogenesis inhibitors vasostatin and interleukin-12, Blood, 96:1900-1905 (2000).
Leong et al.,"Optimized Expression and Specific Activity of IL-12 by Directed Molecular Evolution," *Proc. Natl. Acad. Sci USA.*, vol. 100, No. 3, pp. 1163-1168 (2003).
Kobayashi, et al., "Identification and Purification of Natural Killer Cell Stimulatory Factor (NKSF), a Cytokine with Multiple Biologic Effects on Human Lymphocytes," J. Exp. Med., vol. 170, pp. 827-845 (1989).
Nanni et al., "Combined Allogeneic Tumor Cell Vaccination and Systemic Interleukin 12 Prevents Mammary Carcinogenesis in HER-2/neu Transgenic Mice," *J. Exp. Med.*, vol. 194, pp. 1195-1206 (2001).
Ghazizadeh, et al., "Multiple Classes of Stem Cells in Cutaneous Epithelium: a lineage Analysis of Adult Mouse Skin," *EMBO* 20(6): 1215-22 (2001).
Blanpain, "Skin Regeneration and Repair," *Nature* 464: 686-7 (2010).
Adams et al., "Rotator Cuff Repair Using an Acellular Dermal Matrix Graft: An in Vivo Study in a Canine Model," *Arthroscopy* 22(7): 700-709 (2006).
Dallon et al., Mathmatical modeling of extracellular matrix dynamics using discrete cells: Fiber Orientation and tissue regeneration, *J. Theor. Biol.* 199: 449-471 (1999).
Brancato et al., "Wound Macrophages as Key Regulators of Repair," *Am. J. Pathol.* 178(1), pp. 19-25 (2011).
Rose et al., "Advances in the Treatment of Burn Patients," vol. 23, Suppl. 1, pp. S19-S26 (1997).
Chen et al., "IL-12 Facilitates Both the Recovery of Endogenous Hematopoiesis and the Engraftment of Stem Cells after Ionizing Radiation," vol. 35, No. 2, pp. 202-213 (2007).
Abstract No. 276.2, Pollard et al., IL-12 and IL-18 in combination improve the impaired production of MIP-1α by T cells from thermally insured mice, FASEB J., 15(4), p. A346 (2001).
Ran et al., "Biological Characteristics and Effects of Interleukin12 in Trauma Repair," Chinese Journal of Clinical Rehabilitation, vol. 8, pp. 3345-3347 (2004).
Chiyuki Watanabe, Preoperative treatment of surgical field, Journ. Of Clin. And Exper. Med., vol. 138, p. 388 (1986).
Japanese Office Action issued in related Japanese Patent Application No. 2014-515934, dated Jan. 5, 2016.

\* cited by examiner

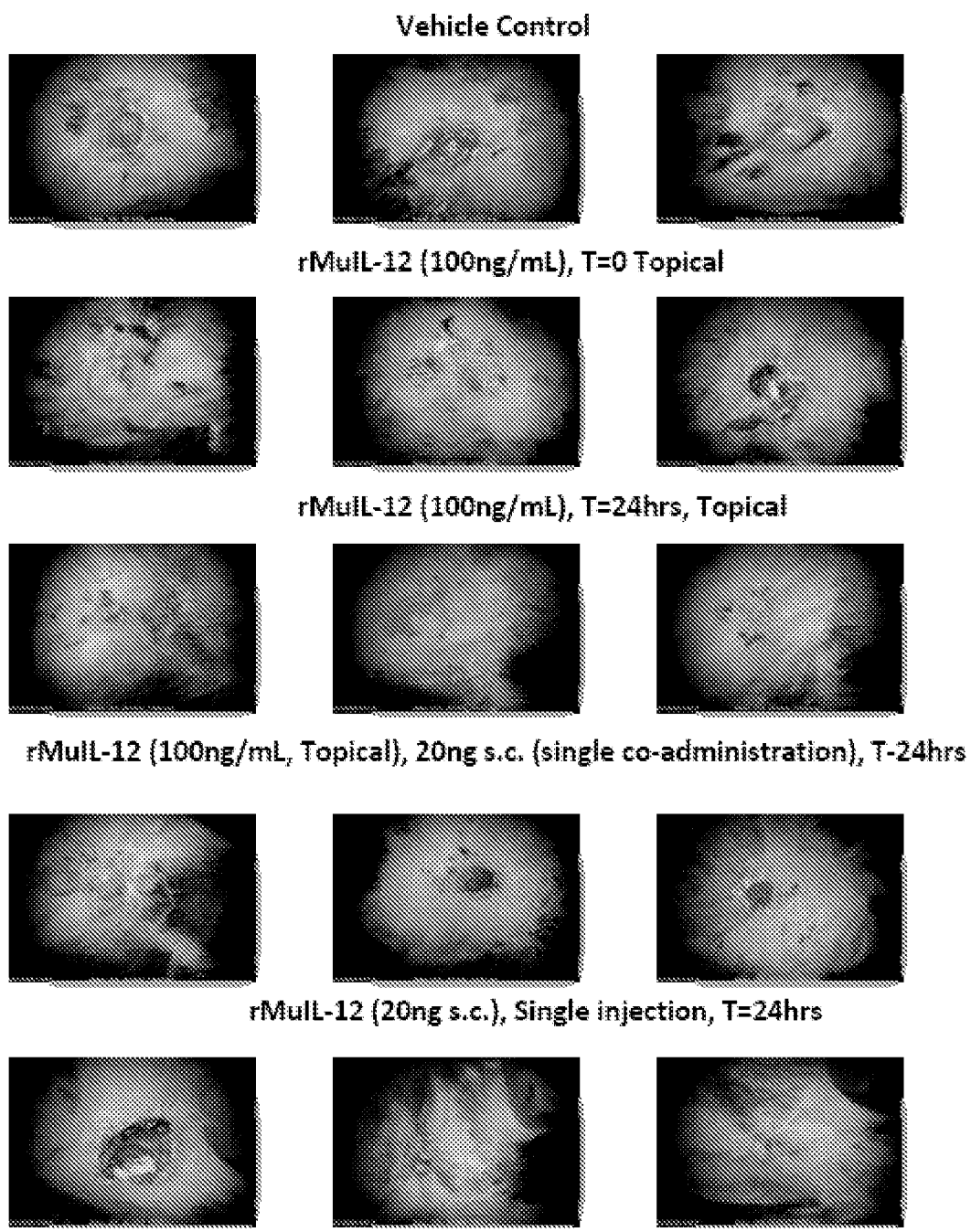

MITIGATION OF CUTANEOUS INJURY WITH IL-12

CROSS-REFERENCE TO RELATED APPLICATIONS

This application claims priority to U.S. Provisional Application Ser. No. 61/496,472, filed Jun. 13, 2011, and U.S. Provisional Application Ser. No. 61/528,053, filed Aug. 26, 2011, each of which are incorporated herein by reference in their entirety, including all figures and tables.

BACKGROUND

Cutaneous wounds represent a major cause of morbidity in diabetics. Every year, 2-3% of diabetics will develop foot ulcers. The lifetime probability of development of a diabetic foot ulcer is between 10 and 15%. In wound injuries that result in limb amputation, up to 90% began with a foot ulcer.

In addition, burn injury is a common cause of morbidity and mortality in the United States, with approximately 100,000 cases of moderate to severe burn injuries requiring hospitalization and 5000 patients dying of burn-related complications each year (Church et al., *Clin Microbiol Rev.*, 19(2):403-34 (2006)).

Reduction of the healing time for cutaneous wounds is highly desirable, as this can reduce the chances of infection and other complications. However, healing of cutaneous injuries is a complex process and can be slowed or interrupted by a variety of other factors, including diabetes, venous or arterial disease, old age, and infection, leading to chronic wounds.

SUMMARY OF INVENTION

In one aspect, the present invention relates to methods for treating a cutaneous wound in a subject, including administrating IL-12 to the cutaneous wound. In some embodiments, the administration is topical, subcutaneous, intramuscular, or any combination thereof. In some embodiments the subject is human.

In some embodiments of the foregoing aspect, the IL-12 is administered topically. In some embodiments the IL-12 is administered topically in a dosage of from about 1 ng/mL up to about 10 μg/mL. In some embodiments, the IL-12 is administered topically in a dosage of from about 10 ng/mL up to about 5 μg/mL. In some embodiments, the IL-12 is administered topically at a dosage of about 100 ng/mL.

In some embodiments of the foregoing aspect, the IL-12 is administered subcutaneously. In some embodiments, the IL-12 is administered subcutaneously in a dosage of from about 10 ng/kg to about 500 ng/kg. In some embodiments, the IL-12 is administered subcutaneously in a dosage of about 80 ng/kg.

In some embodiments, administration of IL-12 results in at least about a 5% increase in wound healing as measured by wound closure, as compared to wound closure observed in the absence of IL-12 administration. In some embodiments, administration of IL-12 results in at least about a 20% increase in wound healing as measured by wound closure, as compared to wound closure observed in the absence of IL-12 administration. In some embodiments, administration of IL-12 results in at least about a 50% increase in wound healing as measured by wound closure, as compared to wound closure observed in the absence of IL-12 administration. In some embodiments, administration of IL-12 results in at least about a 75% increase in wound healing as measured by wound closure, as compared to wound closure observed in the absence of IL-12 administration. In some embodiments, administration of IL-12 results in at least about a 95% increase in wound healing as measured by wound closure, as compared to wound closure observed in the absence of IL-12 administration.

In some embodiments of the foregoing aspect, the subject has been exposed to radiation, which results in a cutaneous wound. In some embodiments, the IL-12 is administered from about 1 hour up to about 24 hours following exposure to radiation resulting in a cutaneous wound.

In some embodiments, the subject is a member of a patient population characterized by an impediment to normal cutaneous wound healing. In some embodiments, the subject is diabetic, elderly, or is an HIV/AIDS patient. In some embodiments, the cutaneous wound is a burn wound. In some embodiments, the cutaneous wound is present at a surgical site. In some embodiments, the IL-12 is administered in conjunction with a skin graft. In some embodiments, the IL-12 is administered in conjunction with acellular or cellular dermal matrices. In some embodiments, the IL-12 is emulsified in a gel matrix. In some embodiments, the gel matrix is isotonic 4% carboxymethylcellulose.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 5B shows a series of photographs (at 1×) of wounds in vehicle-treated and rMuIL-12-treated mice following 9 days of healing.

DETAILED DESCRIPTION OF THE INVENTION

Figure 1A:
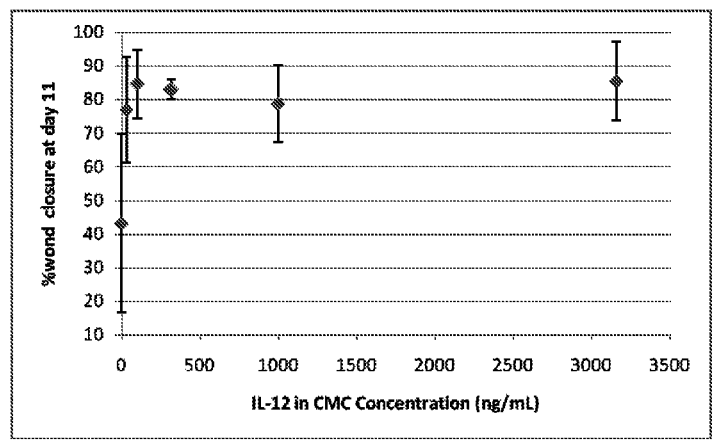
FIG. 1A shows a plot of percent closure of full thickness wounds on day 11 of rMuIL-12 treatment for several concentrations of rMuIL-12.

The present invention is directed to methods of treating cutaneous wounds comprising administration of IL-12 administered to the wound. Administration of the IL-12 is preferably topical, subcutaneous, intramuscularly, or any combination thereof. IL-12 can be used in conjunction with treating any cutaneous wound. Examples of cutaneous wounds include, but are not limited to, cutaneous wounds associated with burns, cutaneous wounds in a patient population characterized by an impediment to normal cutaneous wound healing, such as diabetics, the elderly, and patients with HIV/AIDS, and cutaneous wounds associated with radiation exposure. While not intended to be bound by any theory, the data described herein suggests that IL-12 may contribute to wound healing by stimulation of stem cells within sebaceous glands.

In particular, the present invention is directed to the surprising discovery that IL-12 can accelerate closure of full-thickness skin injuries in a full-thickness injury model of wound healing. This is significant as this type of injury closely mimics the state of a burn wound following surgical debridement and is highly relevant to the use of IL-12 as a therapeutic to enhance wound closure following burn injury.

Moreover, IL-12 can be administered, for example topically and/or subcutaneously, to skin wounds treated with a full-thickness, split-thickness, or composite skin grafts to enhance engraftment and accelerate fusion of the graft to the recipient site and accelerate healing and resolution of the donor site.

IL-12 can be administered topically and/or subcutaneously in conjunction with acellular or cellular dermal matrices. IL-12 stimulates the differentiation and migration of keratinocytes and fibroblasts across a wound bed exposed by a full-thickness cutaneous injury. An acellular dermal matrix over the wound site can provide a structural scaffold for migration and attachment of IL-12 stimulated keratinocytes and fibroblasts.

IL-12 can also be used in conjunction an acellular dermal matrix to treat a tendon or ligament injury, such as rotator cuff injuries. For example, a patient with a full-thickness infraspinatus tendon tear of the rotator cuff can have the defect bridged by placement and suture of an acellular dermal matrix; IL-12 can be applied to the surgical site by methods such as direct injection, infusion of the matrix with IL-12 before implantation, or implantation of a second biodegradable matrix that can deliver IL-12 near the surgical site.

In one embodiment, the methods of the invention, comprising administering IL-12 to a cutaneous wound, result in an about 5% increase in wound healing as measured by wound closure over a specified time period, e.g., such as over a 1, 2, 3, 4, 5, 6, 7, 8, 19, 10, 11, 12, 13, 14, 15, 16, 17, 18, 19, 20, 21, 22, 23, 24, 25, 26, 27, 28, 29, or 30 day time period. In other embodiments, the methods of the invention result in an about 10%, about 15%, about 20%, about 25%, about 30%, about 35%, about 40%, about 45%, about 50%, about 55%, about 60%, about 65%, about 70%, about 75%, about 80%, about 85%, about 90%, about 75%, about 100% improvement in wound healing, as measured by wound closure over a specified time period.

I. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, except where the context requires otherwise, the term "comprise" and variations of the term, such as "comprising," "comprises" and "comprised" are not intended to exclude other additives, components, integers or steps.

As used herein, "Interleukin-12 (IL-12)" refers to any IL-12 molecule that results in improved cutaneous wound healing, including native IL-12 molecules, variant 11-12 molecules and covalently modified IL-12 molecules, now known or to be developed in the future, produced in any manner known in the art now or to be developed in the future. Generally, the amino acid sequences of the IL-12 molecule used in embodiments of the invention are derived from the specific mammal to be treated by the methods of the invention. Thus, for the sake of illustration, for humans, generally human IL-12, or recombinant human IL-12, would be administered to a human in the methods of the invention, and similarly, for felines, for example, the feline IL-12, or recombinant feline IL-12, would be administered to a feline in the methods of the invention. Also included in the invention, however, are certain embodiments where the IL-12 molecule does not derive its amino acid sequence from the mammal that is the subject of the therapeutic methods of the invention. For the sake of illustration, human IL-12 or recombinant human IL-12 may be utilized in a feline mammal. Still other embodiments of the invention include IL-12 molecules where the native amino acid sequence of IL-12 is altered from the native sequence, but the IL-12 molecule functions to yield the hematopoietic properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong S R, et al., *Proc Natl Acad Sci USA.*, 100(3): 1163-8 (Feb. 4, 2003)), where the variant IL-12 molecule is produced by a DNA shuffling method. Also included are modified IL-12 molecules are also included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. No. 4,640,835; 4,496,689; 4,301,144; 4,670,417; 4,791,192 or 4,179,337. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Both native sequence IL-12 and amino acid sequence variants of IL-12 may be covalently modified. Also as referred to herein, the IL-12 molecule can be produced by various methods known in the art, including recombinant methods. Since it is often difficult to predict in advance the characteristics of a variant IL-12 polypeptide, it will be appreciated that some screening of the recovered variant will be needed to select the optimal variant. A preferred method of assessing a change in the hematological stimulating or enhancing properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

The term "IL-12 receptor" is defined herein as a heterodimeric, membrane-bound receptor for the IL-12 ligand. The IL-12 receptor heterodimer subunits are beta 1 (β1) and beta 2 (β2). In accordance with the present invention, the IL-12 receptor may also bind the IL-12 homodimer and the IL-12 monomer, as defined herein, to form a multimer complex comprising the IL-12 ligand/IL-12 receptor pair and the homodimer and/or the monomer. In the present invention, the multimer complex would further activate the IL-12 ligand/IL-12 receptor pair or may modify the activity of the ligand/receptor pair. In accordance with the present invention, the IL-12 receptor protein is defined to be in its endogenous state as isolated from the IL-12 selected stem cell taken from a donor or a patient. As such, the IL-12 receptor may contain polymorphisms distinct from the canonical amino acid sequence of the β1 and β2 subunits.

The term "One or more therapeutically effective dose(s) of IL-12" refers to any dose administered for any time intervals and for any duration that can improve healing of a cutaneous wound.

The term "therapeutically effective amount or dose" is defined herein as a dose of a substance that produces effects for which it is administered. The exact dose of IL-12 will depend on the purpose of the treatment, the timing of administration of IL-12, certain characteristics of the subject to be treated, and the severity of the cutaneous wound, and is ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20$^{th}$ Edition, 2003, Gennaro, Ed., Lippincott, Williams & Wilkins).

Generally, a dose of a therapeutic agent, according to the methods and compositions of the present invention, can be expressed in terms of the total amount of drug to be administered, (i.e., ng, g, or mg). The dose can be expressed as a weight amount of drug administered to a subject (e.g., 20 ng), or as a ratio of the weight amount of drug per volume unit of carrier (e.g., ng/mL), along with the volume of drug and carrier administered (e.g., 1 mL). Alternatively, the dose can be expressed as a ratio of drug to be administered to weight or surface area of subject receiving the administration (i.e., ng/kg, g/kg, ng/m$^2$, or g/m$^2$). When referring to a dose in terms of the mass to be administered per mass of subject (i.e., ng/kg), it will be understood that doses are not equivalent between different animals, and thus conversion factors will need to be used to ensure that one animal receives the same dose equivalent as another animal. Suitable factors for the conversion of a mouse "dose equivalent" for intraperitoneal (i.p.) injection of IL-12 to a "dose equivalent" of a different animal are given in Table 1 below.

TABLE 1

Conversion Factors and Equivalent IL-12 Doses for Several Animals

| Species | Weight (kg) | Total Dose (ng) | Dose (ng/kg) | Dose (ng/m$^2$) | Conversion Factor |
|---|---|---|---|---|---|
| Human | 65 | 25655.82 | 394.7 | 15,000 | 0.0794 |
| Mouse | 0.02 | 99.47 | 4973.44 | 15,000 | 1.0000 |
| Hamster | 0.03 | 130.2 | 4339.87 | 15,000 | 0.8726 |
| Rat | 0.15 | 381.12 | 2540.8 | 15,000 | 0.5109 |
| Guinea Pig | 1.00 | 1335 | 1335 | 15,000 | 0.2684 |
| Rabbit | 2.0 | 2381.1 | 1190.65 | 15,000 | 0.2394 |
| Cat | 2.5 | 2956.44 | 1182.57 | 15,000 | 0.2376 |
| Monkey | 3.0 | 3681.75 | 1227.25 | 15,000 | 0.2468 |
| Dog | 8.0 | 6720 | 840 | 15,000 | 0.1689 |

Thus, in one embodiment, doses are given in terms of mass to surface area (i.e., ng/m$^2$ or g/m$^2$), which are equivalent for all animals. The following basic conversion factors can be used to convert ng/kg to ng/m$^2$: mouse=3.0, hamster=4.1, rat=6.0, guinea pig=7.7, human=38.0 (*Cancer Chemother Repts.*, 50(40):219 (1966)).

The term "cutaneous wound" refers to an injury to the skin of a subject. The wound may be a full-thickness wound, a partial thickness wound, or a wound of only the epidermis. A cutaneous wound may be due to a burn, physical trauma, or surgical trauma.

II. Cutaneous Wound Healing Processes

A. Overview

Wound healing in the skin is a complex phenomenon roughly divided into three phases of inflammation, proliferation, and maturation Innate immune cells, particularly macrophages, play an essential role in the inflammatory and proliferative stages of wound healing. In fact, depletion of macrophages impairs the rate of wound closure (Brancato et al., *Am. J. Pathol.*, 178(1):19-25, 2011).

The inflammatory phase begins with platelet-mediated induction of hemostasis. Platelets secrete several proinflammatory factors that act locally and act as chemoattractants for neutrophils, monocytes, and fibroblasts. It is during this phase that monocytes mature into macrophages which debride the wound and stimulate fibroblasts to synthesize collagen and ground substance of granulation tissue. Macrophages also stimulate the influx of keratinocytes to cover the new skin and endothelial cells for neovascularization.

In the proliferative phase, two to three days after injury, macrophages secrete factors (bFGF, TGFb, and PDGF) to stimulate fibroblasts to begin migrating from the wound edge to contract the wound. Fibroblasts also stabilize and remodel the wound site by organizing collagen molecules into fibers, thereby increasing tensile strength. The fibrin clot begins to resolve leading to a decrease in migration and proliferation of fibroblasts.

During the maturation phase, type II collagen is replaced by type I collagen and epithelial cells cover the wound site until they are contact inhibited. Finally, fibroblasts have differentiated into actin containing myofibroblasts, leading to further contraction of the wound.

B. Cutaneous Wounds in Diabetic Patients

Wound healing in non-diseased individuals results as a consequence of an overlapping and complex interplay between connective tissue formation, cellular proliferation and differentiation, and growth factors. The normal process of wound healing is impeded in diabetics because of deficiencies in the initiation and maintenance of the inflammatory phase of wound healing, ultimately resulting in an impaired cellular proliferation and migration over the wound site. Upregulation of matrix metalloproteinases in diabetic wounds leads to diminishment of growth factors. Finally, diabetics exhibit decreased collagen synthesis and deposition.

Skin wounds on diabetic subjects can be treated using topical and/or subcutaneous dosages of IL-12 to improve wound healing. Preferred topical dosages of IL-12 include 31.6 ng/mL, 100 ng/mL, 316 ng/mL, 1000 ng/mL, and 3160 ng/mL. Such topical doses can be applied at least up to 24 hours following creation of the wound. Subcutaneous dosages of IL-12 can also be applied, either alone or in addition to topical administration of IL-12. Preferred subcutaneous dosages of IL-12 are about 80 ng/kg.

III. Burn Injury

Burns are classified according to five degrees involving the depth of tissue damage and the total body surface area (TBSA) occupied by the wound (Minor=<15% TBSA, Moderate=15-20% TBSA, Major=20% TBSA and above). First degree burns are the least serious generally requiring little more than analgesia for comfort, and typically resolve within a few days. Second degree burns, frequently classified as superficial partial thickness burns, involve damage to the dermis and extends through the epidermis and into the papillary dermis. Second degree burns are typified by the presence of fluid filled blisters. Treatment generally involves the use of analgesics, antibiotics, and bandaging. A more severe second degree burn would extend through the epidermis and into the deep reticular dermis. These types of burns can progress to a third degree status. They often require extensive clinical intervention, have an extended recovery period, and can require debridement and grafting to facilitate healing. Third degree burns extend throughout the entire depth of the dermis. These burns are severe life threatening injuries that require extensive clinical management involving surgical debridement followed by full or partial thickness skin grafting. Scarring is extensive and recovery is lengthy and requires arduous physical therapy to recover function in affected tissues. Finally, fourth degree burns, the most severe, damage extends through the dermis and into the muscle and bone. These injuries frequently require amputation. Because of the loss of the protective epithelial barrier, death from third and fourth degree burns often results from infection.

Topical and subcutaneous dosages of IL-12 can be applied to full-thickness cutaneous wounds, such as severe burn wounds, to improve healing of the wounds. Preferred topical dosages of IL-12 include 31.6 ng/mL, 100 ng/mL, 316 ng/mL, 1000 ng/mL, and 3160 ng/mL. Such topical doses can be applied at least up to 24 hours following creation of the wound. Subcutaneous dosages of IL-12 can also be applied, either alone or in addition to topical administration of IL-12. Preferred subcutaneous dosages of IL-12 are about 80 ng/kg.

A. Second Intention Burn Treatment

While the preferred treatment options for major burns necessitate the use of aggressive use of skin grafting, in minor and moderate second or third degree burns, a preferred method to wound resolution is surgical debridement followed by closure through second intention healing. In this scenario, the wound is managed and the body's natural capacity to heal the wound employed to slowly resolve the wound over time. The protracted time frame required for this method however renders the patient susceptible to infection and can exacerbate scarring.

The examples described herein demonstrate that IL-12 can accelerate closure of full-thickness skin injuries in a full-thickness injury model of wound healing. This type of injury closely mimics the state of a burn wound following surgical debridement and is highly relevant to the use of IL-12 as a therapeutic to enhance wound closure following burn injury.

For example, a patient with minor second or third degree burns may receive surgical debridement of the burn to remove damaged tissue, followed by supportive care. Surgical debridement includes dissection and removal of damaged wound edge epithelium to expose healthy epidermis and dermis. IL-12 is then administered to the wound topically, or subcutaneously at or near the wound site. The wound is covered with a clear permeable bandage to keep it aseptic (i.e., Tegaderm™) and monitored for closure.

B. Use of IL-12 with Skin Grafts

Full-thickness skin grafts are indicated for coverage of deep wounds extending through the dermis such as might be seen in third degree burns and diabetic ulcers, necrotizing fasciitis, etc. Full-thickness grafts consist of the epidermis and much of the underlying dermis. In a typical application, the wound is debrided, an autologous full-thickness graft harvested from healthy tissue and the graft sutured into place. A full-thickness graft is a serious surgical procedure and often not indicated if the patient is seriously impaired from injury or accompanying disease. Full-thickness grafts bring the advantage of an intact wound barrier with accompanying progenitor populations, hair, vasculature, collagen, etc. Disadvantages of using full-thickness skin grafts include insufficient vascular perfusion leading to poor engraftment or rejection if patient condition necessitated the use of an allograft.

Split thickness grafts are frequently used for coverage and healing of burn wounds and other difficult to heal cutaneous injuries. The tissue comprising these grafts are derived from donor sites containing healthy tissue. The graft is harvested by use of a dermatome and comprised of epidermal and some dermal tissue containing keratinocyte progenitors and collagen-producing fibroblasts. The advantage of autologous split-thickness grafts is they can be processed through a meshing apparatus and expanded up to nine times to cover large areas. Re-epithelialization occurs by outgrowth of keratinocytes into the exposed dermis.

Composite grafts are typically smaller grafts that include skin and underlying cartilage tissue. They are often indicated when cartilaginous tissue (nose, ears) have been damaged or destroyed as a consequence of injury. The term is sometimes used to describe human skin equivalents (HSEs) like Apligraf™, which is composed of keratinocytes and fibroblasts on a collagen support matrix.

IL-12 can be administered topically and/or subcutaneously to skin wounds treated with a full-thickness, split-thickness, or composite skin grafts to enhance engraftment and accelerate fusion of the graft to the recipient site and accelerate healing and resolution of the donor site.

C. Use of IL-12 with Acellular and Cellular Dermal Matrices

One approach to the treatment of large cutaneous injuries, such as burn injuries, has been the application of an acellular dermal matrix (e.g. Graftjacket™, Integra™, SkinTemp™). These grafts can either serve as a scaffold to support outgrowth of epidermal keratinocytes or, after implantation be overlayed with an autologous keratinocyte graft that has been generated in vitro.

Cellular dermal matrix, also known as living skin substitute, consists of cultured epidermal autografts or more commonly as "Human Skin Equivalents" (HSEs). HSEs are typically composed of a collagen support matrix overlayed with living allogeneic fibroblasts and/or keratinocytes derived from male foreskin donors. Exemplary products include Apligraf™ (Organogenesis, Inc., Canton Mass.), Dermagraft™ (Advanced BioHealing, Westport, Conn.), Gintuit™ (Organogenesis, Inc., Canton Mass.), and Orcel™ (Forticell Bioscience, Englewood Cliffs, N.J.). Composited HSEs such as Apligraf™ have been successfully used under compassionate use for critically burned patients. Another example of living skin substitutes includes Epicel™ (Genzyme Biosurgery), which is made up of sheets of autologous keratinocytes cultured ex vivo (2 to 8 cell layers thick). These HSEs are used to treat diabetic skin ulcers, burns, and to infill receded gum lines.

IL-12 can be administered topically and/or subcutaneously in conjunction with acellular or cellular dermal matrices. IL-12 stimulates the differentiation and migration of keratinocytes and fibroblasts across a wound bed exposed by a full-thickness cutaneous injury. An acellular dermal matrix over the wound site can provide a structural scaffold for migration and attachment of IL-12 stimulated keratinocytes and fibroblasts.

IL-12 can also be used in conjunction an acellular dermal matrix to treat rotator cuff injuries. Adams et al., *Arthroscopy*, 22(7): 700-709 (2006). For example, a patient with a full-thickness infraspinatus tendon tear of the rotator cuff can have the defect bridged by placement and suture of an acellular dermal matrix; IL-12 can be applied to the surgical site by methods such as direct injection, infusion of the matrix with IL-12 before implantation, or implantation of a second biodegradable matrix that can deliver IL-12 near the surgical site.

The following examples are given to illustrate the present invention. It should be understood, however, that the invention is not to be limited to the specific conditions or details described in these examples.

D. Enhanced Cosmetic Remodeling

Delayed healing can result in scarring when collagen is deposited in symmetrically cross-linked fibers rather than in the basket weave pattern associated with non-injured skin (Dallon et al., Mathmatical modeling of extracellular matrix dynamics using discrete cells: Fiber orientation and tissue regeneration, J. Theor. Biol. 199:449-471, 1999). In almost all instances, scarring is a normal consequence of healing of skin injuries. Accelerated wound closure diminishes scar formation by limiting the time required for aberrant collagen deposition. The pattern of aligned collagen deposition results in diminished wound strength and blocks the repopulation of the injured tissue with new sweat glands and hair follicles. In addition, scars can present cosmetic challenges when they manifest in exposed area such as the face. The type and severity of injury, coupled with underlying genetics of the individual, can lead to the development of hypertrophic (raised), atrophic (sunken), or keloid (large, benign, tumorous) scars. Patients with wounds that have closed via secondary intention healing often manifest hypertrophic or keloid scars as a result of delayed healing. Current therapies concentrate on the use of post-scarring surgical interventions such as chemical peals, dermabrasion, fillers (Artefill™, i.e., bovine collagen and polymethylmethacrylate, Radiesse™, Dermatix™ (silicone gel)), lasers, and radiation (reduction of keloid scars). Only 1 injectible drug (corticosteroid) is approved for the treatment of appearance of keloid scars. Clinical trials are under underway for the assessment of an interventional drug for the suppression or prevention of scars. Avotermin (Juvista™, rTGFβ3) is a drug being investigated for the suppression of split-thickness graft scarring and other surgical scars (Occleston, et al., 2011; So et al., 2011; Durani, et al., 2008).

Topical or subcutaneous administration of IL-12 in patients with cutaneous injuries diminishes scar formation, enhances wound strength and UV resistance, and improves cosmetic appearance by accelerating the rate of wound closure. In addition, IL-12 diminishes delayed wound closure by suppression of cutaneous infections. Thus, IL-12 may be administered subcutaneously in the range of about 15,000 ng/m² to diminish delays in wound closure.

IV. Timing of IL-12 Administration

Advantageously, as provided by the methods of the present invention, administration of IL-12 may occur during any suitable time period following a cutaneous wound.

In one embodiment, where the cutaneous wound is associated with exposure to radiation, IL-12 can be administered any time after radiation exposure up to and including about a week after exposure. Although the total dose of radiation will factor into the time period in which IL-12 should be administered, according to one embodiment, IL-12 may be administered at any time up to about 120 hours following exposure to radiation resulting in a cutaneous injury. In other embodiments, IL-12 can be administered at any time up to about 96 hours post-irradiation, up to about 72 hours post-irradiation, or at a time up to about 60 hours, about 48 hours, about 36 hours, about 24 hours, about 18 hours, about 12 hours, about 8 hours, about 6 hours, or less following exposure to radiation resulting in a cutaneous injury. In one specific embodiment, IL-12 is administered to a subject in need thereof between a range of about 1 hour to about 72 hours after exposure to ionizing radiation. In another embodiment, IL-12 is administered between a range of about 1 hour and about 24 hours after exposure, or between a range of about 6 hours and about 24 hours following exposure to an acute dose of whole body ionizing radiation.

IL-12 can be administered at any time point after radiation exposure resulting in a cutaneous wound. In one embodiment of the invention, IL-12 is administered at least about 24 hours or more following exposure to radiation. Other time points for administration following radiation exposure resulting in a cutaneous wound include about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 1.5 days, about 2 days, about 2.5 days, about 3 days, about 3.5 days, about 4 days, about 4.5 days, about 5 days, about 5.5 days, about 6 days, about 6.5 days, about 7 days, or about any combination thereof with multiple IL-12 administrations (e.g., at 12 hours and 48 hours.

V. IL-12 Dosing and Dosages

Generally the IL-12 doses used in the methods for treating cutaneous wounds will be high enough to be effective for the treatment of a cutaneous wound, but low enough to mitigate negative side effects associated with IL-12 administrations, including for example, radiosensitivity of the GI tract (associated with radiation exposure) and IFN-γ up-regulation.

In one aspect, a single dose of IL-12 is sufficient to confer improved cutaneous wound healing. In other aspects, IL-12 may be administered in more than one dose, such as about 2, about 3, about 4, about 5 or more doses.

Accordingly, in one aspect, the present invention provides a method for treating cutaneous wounds, including improving mitigation of cutaneous wounds, comprising the administration of a dose of IL-12 to a subject having cutaneous wound. In one embodiment, the dose of IL-12 is less than about 100 μg/m². In another embodiment, the dose of IL-12 is less than about 75 μg/m², or less than about 400 ng/kg (15 μg/m²). In another embodiment, the dose can be between about 1 μg/m² and about 100 μg/m². Other exemplary IL-12 dosages include less than 1 μg/m² or about 1 μg/m², less than about 3 μg/m² or about 3 μg/m², less than about 4 μg/m² or about 4 μg/m², less than about 5 μg/m² or about 5 μg/m², less than about 6 μg/m² or about 6 μg/m², less than about 7 μg/m² or about 7 μg/m², less than about 8 μg/m² or about 8 μg/m², less than about 9 μg/m² or about 9 μg/m², less than about 10 μg/m² or about 10 μg/m², less than about 11 μg/m² or about 11 μg/m², less than about 12 μg/m² or about 12 μg/m², less than about 15 μg/m² or about 15 μg/m², less than about 20 μg/m² or about 20 μg/m², less than about 25 μg/m² or about 25 μg/m², less than about 30 μg/m² or about 30 μg/m², less than about 35 μg/m² or about 35 μg/m², less than about 40 μg/m² or about 40 μg/m², less than about 45 μg/m² or about 45 μg/m², less than about 50 μg/m² or about 50 μg/m², less than about 55 μg/m² or about 55 μg/m², less than about 60 μg/m² or about 60 μg/m², less than about 65 μg/m² or about 65 μg/m², less than about 70 μg/m² or about 70 μg/m², less than about 75 μg/m² or about 75 μg/m², less than about 80 μg/m² or about 80 μg/m², less than about 85 μg/m² or about 85 μg/m², less than about 90 μg/m² or about 90 μg/m², less than about 95 μg/m² or about 95 μg/m², less than about 100 μg/m² or about 100 μg/m², less than about 900 ng/m² or about 900 ng/m², less than about 800 ng/m² or about 800 ng/m², less than about 700 ng/m² or about 700 ng/m², less than about 600 ng/m² or about 600 ng/m², less than about 500 ng/m² or about 500 ng/m², less than about 400 ng/m² or about 400 ng/m², less than about 300 ng/m² or about 300 ng/m², less than about 250 ng/m² or about 250 ng/m², less than about 200 ng/m² or about 200 ng/m², less than about 100 ng/m² or about 100 ng/m², and all doses in-between.

In one embodiment of the invention, the dosage of IL-12 is between about 1 ng/mL and about 10 μg/mL. In another embodiment, the dosage of IL-12 is between about 10 ng/mL and about 5 μg/mL. In other embodiments of the invention, the dosage of IL-12 is about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, or about 400 ng/mL.

In one embodiment of the invention, the dosage of IL-12 is between about 10 ng/kg and about 500 ng/kg. In other embodiments of the invention, the dosage of IL-12 is about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, or about 400 ng/kg.

When administered in multiple doses, i.e. two, three, four, or more, the first IL-12 dose and subsequent IL-12 dose(s) can be equivalent doses, or they can be different dose amounts. For example, in certain embodiments, subsequent dose(s) can be administered at about 90% of the initial dose, or at about 80%, about 75%, about 70%, about 60%, about 50%, about 40%, about 30%, about 25%, about 20%, or about 10% or less of the original dose.

VI. IL-12 Compositions

For general descriptions relating IL-12, see U.S. Pat. Nos. 5,573,764, 5,648,072, 5,648,467, 5,744,132, 5,756,085, 5,853,714 and 6,683,046. Interleukin-12 (IL-12) is a heterodimeric cytokine generally described as a proinflamatory cytokine that regulates the activity of cells involved in the immune response (Fitz et al., *J. Exp. Med.*, 170: 827-45 (1989)). Generally IL-12 stimulates the production of interferon-γ (IFN-γ) from natural killer (NK) cells and T cells (Lertmemongkolchai et al., *J. of Immunology*, 166: 1097-105 (2001); Cui et al., *Science*, 278:1623-6 (1997); Ohteki et al., *J. Exp. Med.*, 189:1981-6 (1999); Airoldi et al., *J. of Immunology*, 165: 6880-8 (2000)), favors the differentiation of T helper 1 (TH1) cells (Hsieh et al., *Science*, 260: 547-9 (1993); Manetti et al., *J. Exp. Med.*, 177: 1199-1204 (1993)), and forms a link between innate resistance and adaptive immunity. IL-12 has also been shown to inhibit cancer growth via its immuno-modulatory and anti-angiogenesis effects (Brunda et al., *J. Exp. Med.*, 178: 1223-1230 (1993); Noguchi et al., *Proc. Natl. Acad. Sci. U.S.A.*, 93: 11798-11801 (1996); Giordano et al., *J. Exp. Med.*, 194: 1195-1206 (2001); Colombo et al., *Cytokine Growth factor, Rev.* 13: 155-168 (2002); Yao et al., *Blood*, 96: 1900-1905 (2000)). IL-12 is produced mainly by dendritic cells (DC) and phagocytes (macrophages and neutrophils) once they are activated by encountering pathogenic bacteria, fungi or intracellular parasites (Reis et al., *J. Exp. Med.*, 186:1819-1829 (1997); Gazzinelli et al., *J. Immunol.*, 153: 2533-2543 (1994); Dalod et al., *J. Exp. Med.*, 195: 517-528 (2002)). The IL-12 receptor (IL-12 R) is expressed mainly by activated T cells and NK cells (Presky et al., *Proc. Natl. Acad. Sci. U.S.A.*, 93: 14002-14007 (1996); Wu et al., *Eur. J. Immunol.*, 26: 345-50 (1996)).

Generally the production of IL-12 stimulates the production of IFN-γ, which, in turn, enhances the production of IL-12, thus forming a positive feedback loop. In in vitro systems, it has been reported that IL-12 can synergize with other cytokines (IL-3 and SCF for example) to stimulate the proliferation and differentiation of early hematopoietic progenitors (Jacobsen et al., *J. Exp. Med.*, 2: 413-8 (1993); Ploemacher et al., *Leukemia*, 7: 1381-8 (1993); Hirao et al., *Stem Cells*, 13: 47-53 (1995)).

In certain embodiments, the IL-12 is a mammalian IL-12, recombinant mammalian IL-12, murine IL-12 (mIL-12), recombinant murine IL-12 (rmIL-12), human IL-12 (hIL-12), recombinant human IL-12 (rhIL-12), canine IL-12 or rIL-12, feline IL-12 or rIL-12, bovine IL-12 or rIL-12, equine IL-12 or rIL-12, or biologically active variants or fragments thereof. In one specific embodiment, the rhIL-12 is HemaMax™ (Neumedicines Inc.). In certain embodiments, the IL-12 can be modified in a fashion so as to reduce the immunogenicity of the protein after administration to a subject. Methods of reducing the immunogenicity of a protein are well known in the art and include, for example, modifying the protein with one or water soluble polymers, such as a PEG, a PEO, a carbohydrate, a polysialic acid, and the like.

It is well known that solutions of proteins that are formulated at low concentrations are susceptible to loss of a significant fraction of the protein prior to administration. One major cause of this problem is adsorption of the protein on the sides of tubes, vials, syringes, and the like. Accordingly, in certain aspects, when administered at low or ultralow doses, it will be beneficial to administer IL-12 along with a suitable carrier molecule or bulking agent. In one embodiment, the carrier agent may be a protein suitable for pharmaceutical administration, such as albumin. Generally, the carrier molecule or protein will be present in the formulation in excess of IL-12 to minimize the amount of IL-12 lost prior to administration. In certain embodiments, the carrier will be present at a concentration of at least about 2 times the concentration of IL-12, or at a concentration of at least about 3, at least about 4, at least about 5, at least about 6, at least about 7, at least about 8, at least about 9, at least about 10, at least about 25, at least about 50, at least about 100, or more times the concentration of IL-12 in the formulation.

IL-12 composition provided herein and used according to the methods of the invention can be formulated for administration via any known method, but preferably topically, subcutaneously, or intramuscularly. Further, an efficacious dose of IL-12 may differ with different routes of administration.

In some embodiments, the formulations provided herein further comprise one or more pharmaceutically acceptable excipients, carriers, and/or diluents. In addition, the formulations provided herein may further comprise other medicinal agents, carriers, adjuvants, diluents, tissue permeation enhancers, solubilizers, and the like. Methods for preparing compositions and formulations for pharmaceutical administration are known to those skilled in the art (see, for example, REMINGTON'S PHARMACEUTICAL SCIENCES, 18$^{TH}$ ED., Mack Publishing Co., Easton, Pa. (1990)). Formulations used according to the methods of the invention may include, for example, those taught in U.S. Pat. No. 5,744,132, which is hereby incorporated by reference in its entirety for all purposes.

EXAMPLES

Example 1: Topical Administration of rMuIL-12 to Full-Thickness Cutaneous Wounds To study the effect of IL-12 on full-thickness skin wounds, mice with full thickness skin wounds were treated topically with different amounts of rMuIL-12. Full-thickness cutaneous injuries, which are equivalent to a third degree burn, are a challenging and commonly used model for the study of the mechanisms of wound healing, as well as the examination of potential treatments for accelerating or enhancing resolution of normal or diseased wounds.

Materials & Methods 18 mice were divided into six treatment groups of 3 animals each. The treatment groups are listed in Table 2 below.

TABLE 2

Treatment Groups for Topical IL-12 Administration

| Group | Treatment |
| --- | --- |
| 1 | CMC (4%) Alone |
| 2 | CMC (4%) + 31.6 ng/mL rMuIL-12 |
| 3 | CMC (4%) + 100 ng/mL rMuIL-12 |
| 4 | CMC (4%) + 316 ng/mL rMuIL-12 |
| 5 | CMC (4%) + 1000 ng/mL rMuIL-12 |
| 6 | CMC (4%) + 3160 ng/mL rMuIL-12 |

*CMC = carboxymethylcellulose

A circular 8.0 mm diameter wound was induced in anesthetized mice using an 8 mm biopsy punch and the epidermal layer was removed to expose the underlying tissue. Recombinant murine IL-12 (rMuIL-12) (SBH Biosciences) was emulsified in a sterile isotonic gel matrix consisting of 4% carboxymethylcellulose (CMC) in Dulbecco's Phosphate Buffered Saline (DPBS). Benzoin tincture was applied peripherally around the wound site and a Tegaderm™ dressing was applied over the wound site. The wound site for each mouse was then filled to capacity with control (CMC alone) or CMC+rMuIL-12 gel matrix using an 18 gauge syringe needle (approximately 150 µL). A 1.0 mL syringe (Terumo, Slip-Tip #SS-01T) was used for delivery of the CMC and CMC/rMuIL-12. The syringe is graduated in 10 µl increments. Delivered volumes are apparent by noting level on graduations. No external dressing was applied over the Tegaderm™ dressing. The gel matrix under the dressing was replenished at 2 days and 7 days following wound creation and initial application of the gel matrix.

Wound areas were quantified by overlaying the wound site with a glass slide and tracing the wound margin onto the slide with a black pen. The slides were scanned as a JPEG image and imported into Photoshop CS™. The number of pixels comprising the wound area was determined and converted into an area of square millimeters (calculated area of wound=50.24 mm$^2$, 8 mm diameter full-thickness wound, $\pi r^2$). Wound area was measured five times, at two to three day intervals.

On the eleventh day of the study, blood samples were collected and examined for lymphocyte counts and levels of IL-12 and IFN-λ. In addition, the wound site was collected at Day 11 and stained with Mallory's trichrome for histologic examination. Trichrome staining is the standard for visualization of stage of remodeling of cutaneous wounds following injury.

Results

Figure 1B:
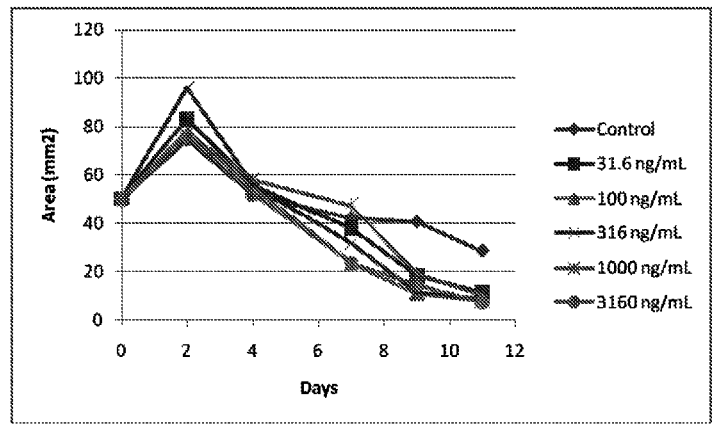
FIG. 1B shows a graph of changes in wound area over time (in days) for mice treated with various concentrations of rMuIL-12.
Figure 1C:
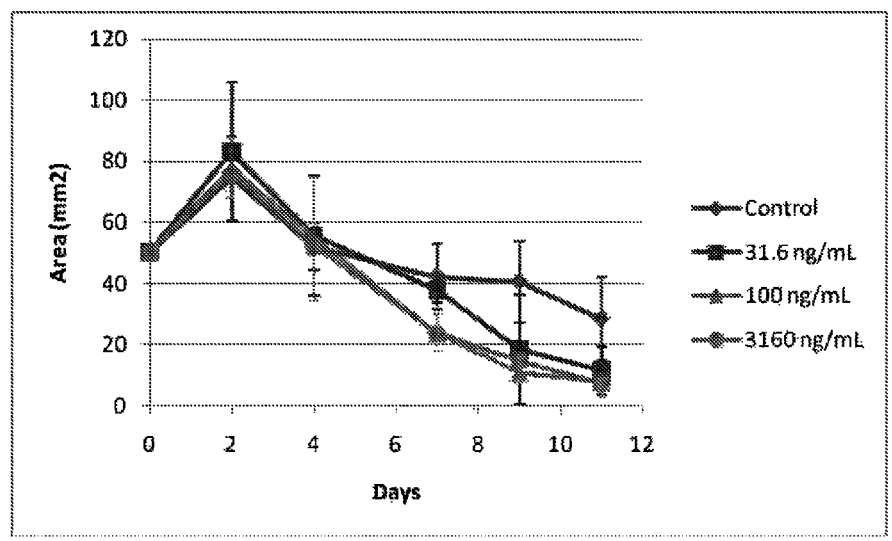
FIG. 1C shows part of the data in FIG. 1B along with error bars, including control, 31.6 ng/mL, 100 ng/mL, and 3160 ng/mL dosages.

Maximal healing 11 days following wound creation and topical rMuIL-12 application occurred at a dose of 100 ng/mL, and did not increase with increasing doses of rMuIL-12 (FIG. 1A). All groups treated with CMC+rMuIL-12 showed a greater percentage of wound closure as compared with CMC control matrix by days 9 and 11 (FIG. 1B). Data for the control and only three of the dosages in FIG. 1B (31.6 ng/mL, 100 ng/mL, and 3160 ng/mL) are shown in FIG. 1C. Table 3 below shows p-values of wound area compared with control for days 2, 4, 7, 9, and 11 (bolded numbers are $p<0.05$). The 100 ng/mL rMuIL-12 group showed a statistically significant reduction in wound area at days 7, 9, and 11 (by t-test; $p<0.05$) compared to the control group. Statistically significant reductions in wound area were also observed for the 31.6 ng/mL dose at day 11, and for the 3160 ng/mL dose at days 9 and 11. Without being held to any particular theory, the lack of statistical significance from control at doses of 316 ng/mL and 1000 ng/mL are likely due to the small number of mice (three) in each of the groups.

TABLE 3

Statistical Significance of Wound Area Treated with IL-12 vs. Control

| Day | rMuIL-12 (31.6 ng/mL) | rMuIL-12 (100 ng/mL) | rMuIL-12 (316 ng/mL) | rMuIL-12 (1000 ng/mL) | rMuIL-12 (3160 ng/mL) |
|---|---|---|---|---|---|
| 2 | 0.1215 | 0.381627 | 0.55888 | 0.34026 | 0.428741 |
| 4 | 0.342364 | 0.437305 | 0.263721 | 0.059673 | 0.496804 |
| 7 | 0.246345 | 0.012142 | 0.326977 | 0.262902 | 0.086662 |
| 9 | 0.101027 | 0.018461 | 0.121607 | 0.057338 | 0.012446 |
| 11 | 0.035108 | 0.046694 | 0.181913 | 0.10688 | 0.022395 |

No changes in blood cell counts for animals treated with CMC+rMuIL-12 were observed, although a trend towards increases in lymphocytes was observed. ELISA for IL-12 and IFN-λ showed no detection of either cytokine in plasma of treated or control mice.

Figure 2A:
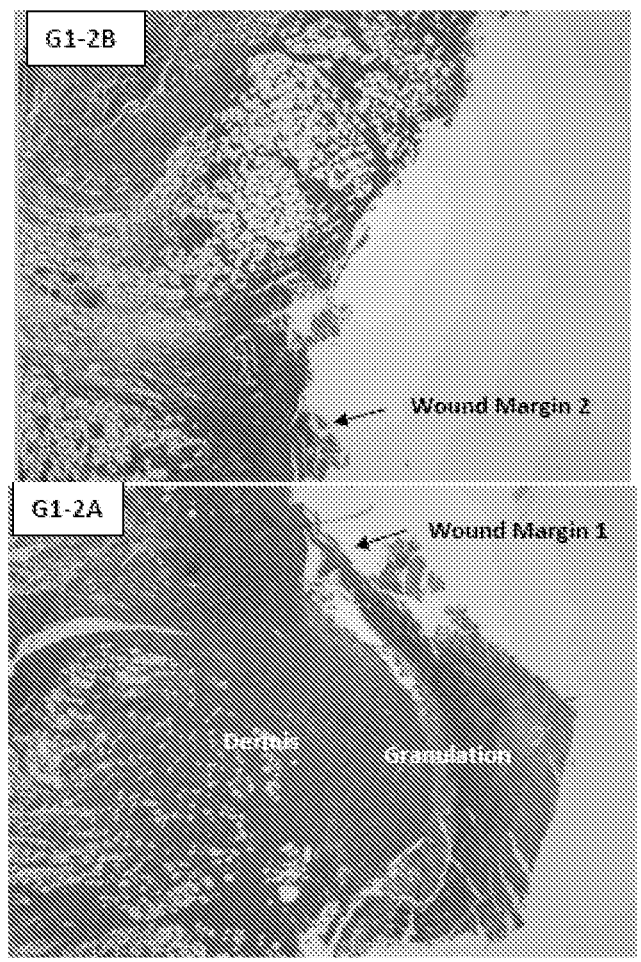
FIG. 2A shows a photomicrograph of trichrome-stained tissue sections of wound sites at 40×, from full-thickness injuries treated with vehicle alone. The large area of granulation tissue is noted in the photomicrograph, as well as the location of the wound margin and dermis.
Figure 2B:
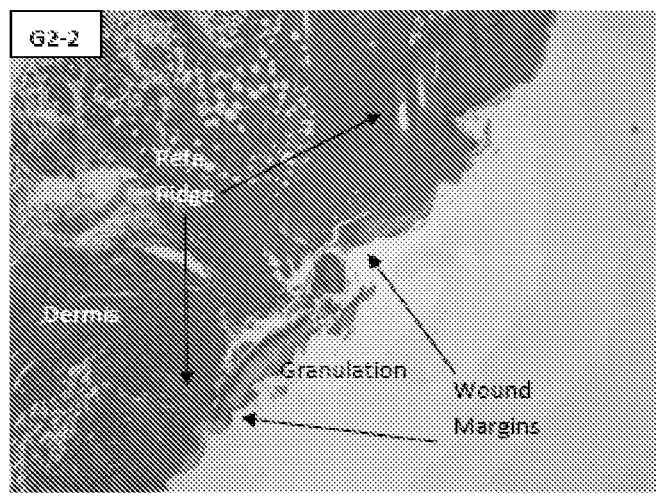
FIGS. 2B and 2C show photomicrographs (40×) of trichrome-stained tissue sections of wound sites from mice treated with vehicle and 31.6 ng/mL rMuIL-12.
Figure 2C:
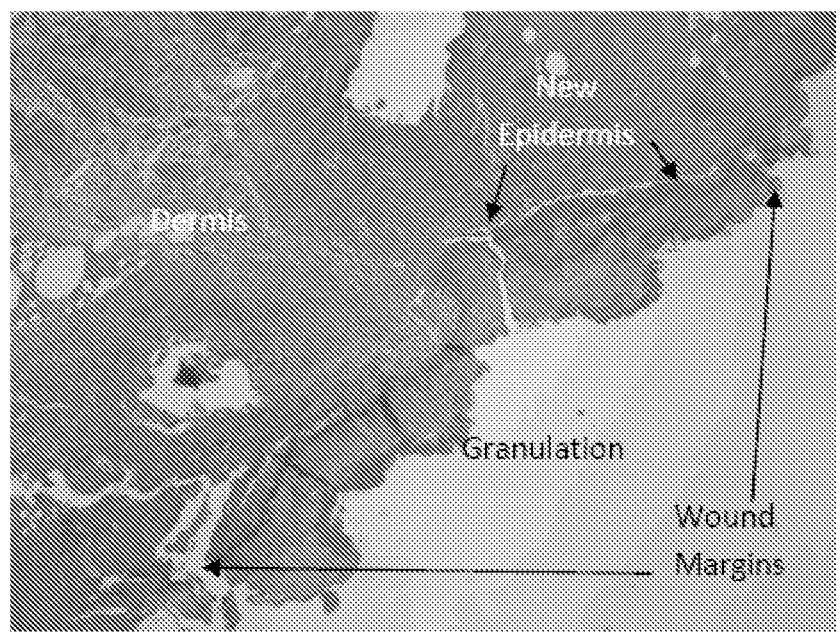

FIG. 2A shows contiguous micrographs of trichrome-stained tissue sections of wound sites at 40×, from full-thickness injuries treated with vehicle alone. The large area of granulation tissue is noted in the micrograph, as well as the location of the wound margin and dermis. FIGS. 2B and 2C show micrographs (40×) of trichrome-stained tissue sections of wound sites from mice treated with vehicle and 31.6 ng/mL rMuIL-12. The presence of rete ridges is indicated in FIG. 2B, indicative of maturing epidermis. New epidermis is indicated in FIG. 2C, along with some granulated tissue.

Example 2: Expression of IL-12Rβ2 in Wounds of Irradiated Mice

A study was undertaken to examine the level, distribution, and timing of expression of IL-12Rβ2 in full-thickness cutaneous injuries topically treated with vehicle alone or vehicle+rMuIL-12.
Materials and Methods Thirty-six mice received 500 cGy of total body irradiation in a Gammacell® 40 irradiator. The mice were then anesthetized and given a circular 10.0 mm diameter wound using a biopsy punch. The mice were then split into two groups, with one group treated with 4% CMC alone, and the second group receiving 4% CMC+100 ng/mL of rMuIL-12. Wound treatment and measurement are as described in Example 1 (calculated area of wound=78.5 mm$^2$, 10 mm diameter full-thickness wound, $\pi r^2$).

Mice were then sacrificed and their wounds removed, sectioned in paraffin, and fixed in formalin at various time points following wound initiation and treatment with rMuIL-12. The fixed tissue was deparaffinized with xylene, hydrated in ethanol, and washed in water.

For antigen retrieval and staining, the tissue sections were immersed in 1×HIER buffer (heat induced epitope retrieval) and heated in a pressure cooker for 10 minutes. Peroxidases and non-specific proteins were then blocked using 0.3% hydrogen peroxide and Background Sniper™ reagent (Biocare Medical, Concord, Calif.), respectively. The treated tissue sections were then stained with rabbit anti-human IL-12Rβ2, detected using a horseradish peroxidase-based secondary antibody detection system (ImmPRESS anti-rabbit IgG and ImmPact AEC substrate; Vector Laboratories, Burlingame, Calif.). The tissue sections were also counterstained with hematoxylin.
Results Examination of skin wounds from irradiated mice showed that IL-12Rβ2 expression is upregulated regardless of exposure to rMuIL-12, a unique finding not previously described. There is no apparent effect of IL-12 treatment on expression of IL-12Rβ2 in irradiated skin. IL-12Rβ2, upregulated as a consequence of injury, exists in a ready state waiting to trigger a wound healing cascade in response to endogenous or exogenous administration of IL-12.

Figure 3A:
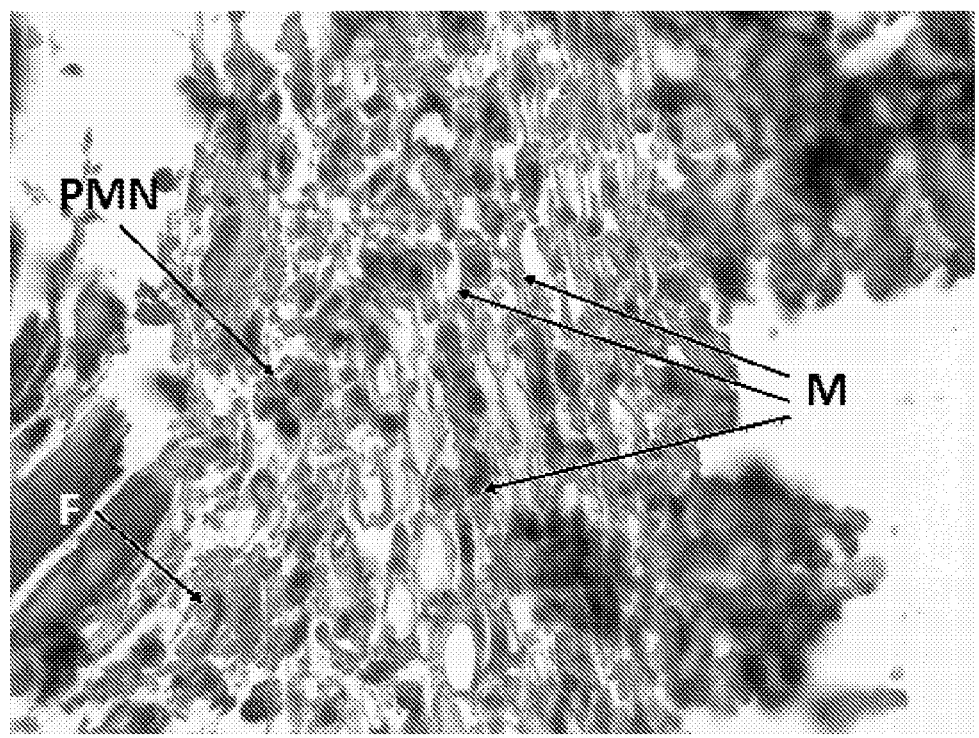
FIG. 3A shows a photomicrograph of IL-12Rβ2 expression in the dermis of a cutaneous wound from an irradiated mouse (3 days post-injury). M=macrophages, PMN=polymorphonuclear leukocytes, F=fibroblasts.

In dermis, the majority of IL-12Rβ2 expression is in macrophages, consistent with observations of other researchers. FIG. 3A shows a photomicrograph of IL-12Rβ2 expression in the dermis of a cutaneous wound from an irradiated mouse (3 days post-injury; M=macrophages, PMN=polymorphonuclear leukocytes, F=fibroblasts). Polymorphonuclear leukocytes (PMNs) and fibroblasts (identified morphologically) also express IL-12Rβ2 but these cell types are in the minority at 3 days after injury.

Figure 3B:
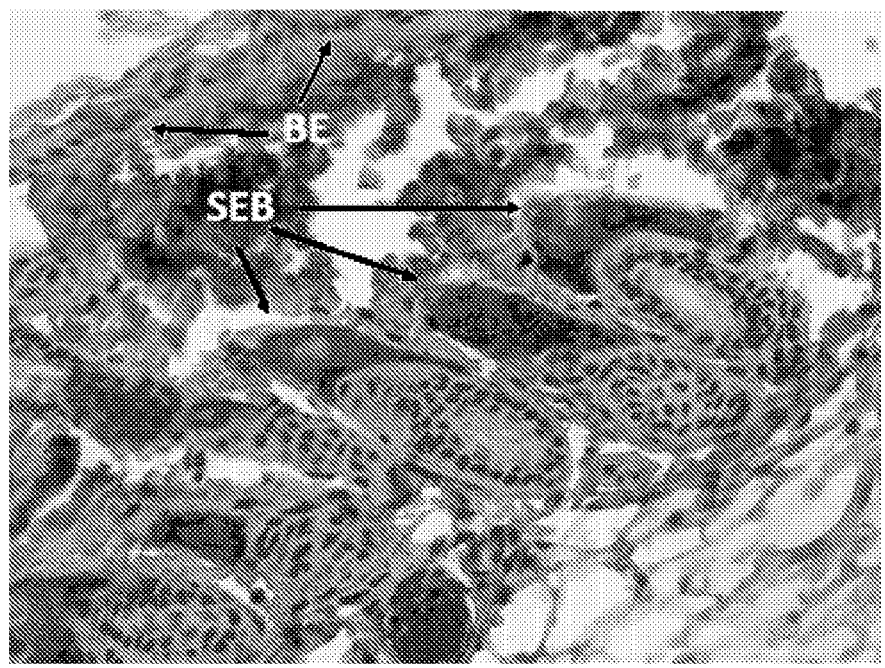
FIG. 3B shows a photomicrograph of IL-12Rβ2 expression in the sebaceous gland (SEB) and basal epidermis (BE) from a cutaneous wound of an irradiated mouse.
Figure 3C:
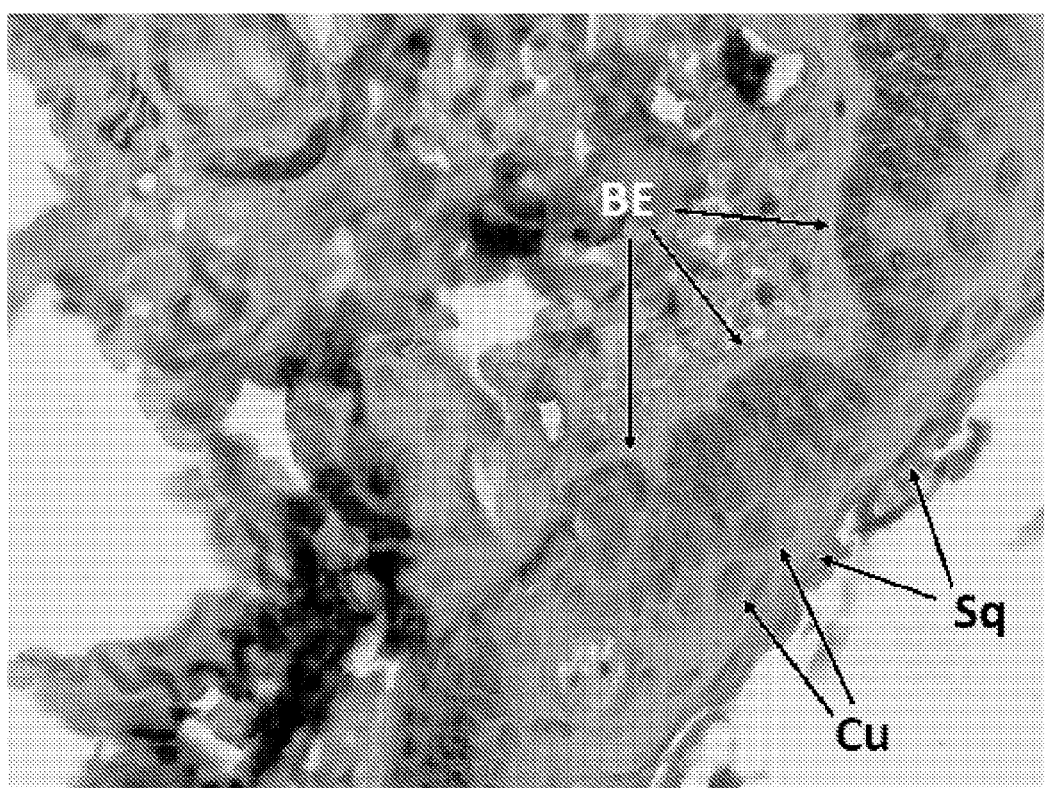
FIG. 3C shows a photomicrograph of IL-12Rβ2 expression in the stratum basale (BE), cuboidal cells (Cu) of the stratum spinosum, and squamous cells (Sq) in the stratum granulosum.

The majority of IL-12Rβ2 expression in the epidermis is in the cells comprising the basal membrane, as well as in the sebaceous glands of wounded skin (see FIG. 3B). Stem cells known to be contained in sebaceous glands have been described as contributing to re-epithelialization of wounded tissue (Ghazizadeh and Taichman, EMBO 20(6):1215-22 (2001); Blanpain, Nature 464:686-7 (2010)). Given the high level of IL-12Rβ2 expression in the sebaceous glands of wounded skin, IL-12 may contribute to wound healing by stimulation of stem cells within sebaceous glands. In fact, multipotent stem cells derived from sebaceous glands are being used to rapidly create human skin substitutes for wound grafts. FIG. 3C shows a photomicrograph of IL-12Rβ2 expression in the stratum basale (BE), cuboidal cells (Cu) of the stratum spinosum, and squamous cells (Sq) in the stratum granulosum.

Example 3: Mitigation of Skin Wounds in Irradiated Mice Using IL-12

Figure 4A:
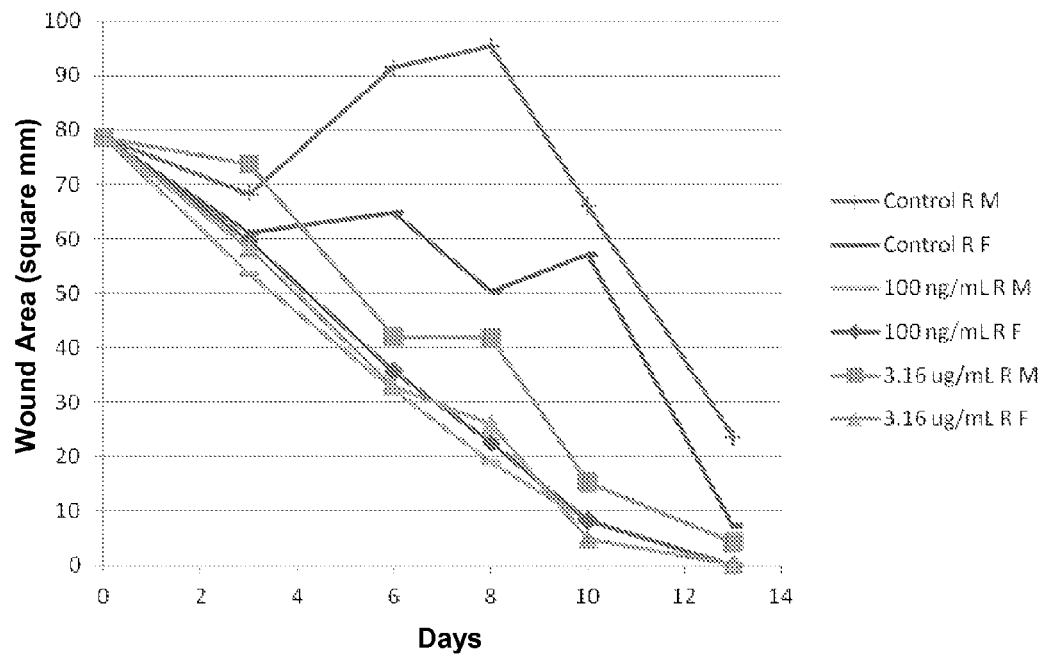
FIG. 4A is a graph of changes in wound area over time (in days) for irradiated mice treated with various concentrations of rMuIL-12 (R M=male mice; R F=female mice).
Figure 4B:
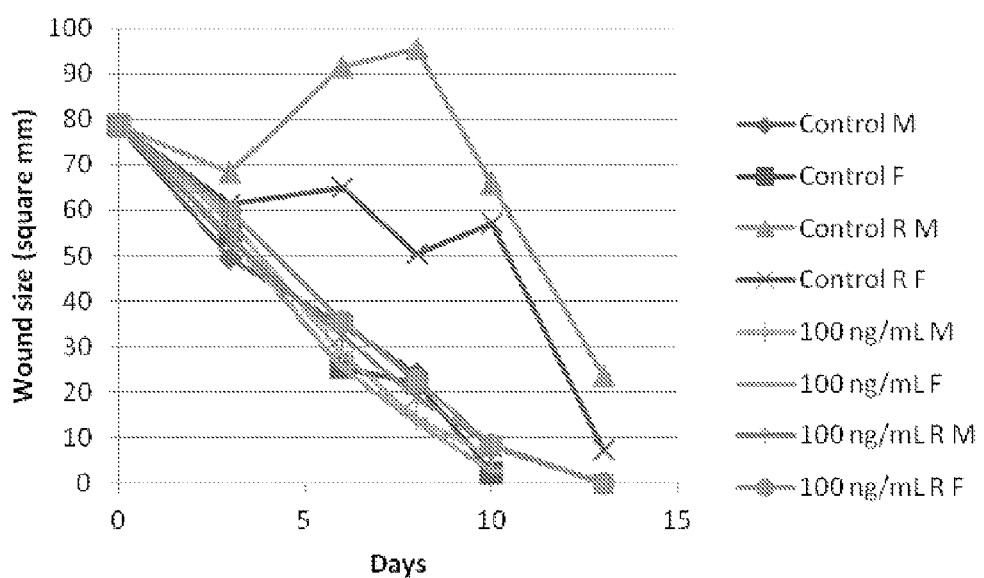
FIG. 4B is graph of data from FIG. 4A, only for irradiated mice that received 100 ng/mL of rMuIL-12.

A study was undertaken to examine the healing of full-thickness cutaneous injuries in irradiated mice that were topically treated with vehicle alone or vehicle+rMuIL-12.
Materials and Methods Eighteen mice received 500 cGy of total body irradiation in a Gammacell® 40 irradiator, as described in Example 2. The mice were then anesthetized and given a circular 10.0 mm diameter wound using a biopsy punch. The mice were then divided into three treatment groups: Group 1 was treated with 4% CMC alone; Group 2 was treated with 4% CMC+100 ng/mL of rMuIL-12; and Group 3 was treated with 4% CMC+3160 ng/mL of rMuIL-12. Wounds were covered with Tegaderm as described in Example 1. Approximately 150 µl of CMC was delivered to each wound. This volume represents an approximate rMuIL-12 wound dosage of 15 ng (for 100 ng/mL concentration) or 474 ng (for 3160 ng/mL concentration). Wound measurement are as described in Example 1 (calculated area of wound=78.5 mm$^2$, 10 mm diameter full-thickness wound, $\pi r^2$).
Results Wound closure of all treated and control mice is shown in the graph of FIGS. 4A and 4B. 50% wound closure ($T_{50}$) in rMuIL-12-treated (100 ng/mL) irradiated male and female mice was observed at days 5-6 and 75% wound closure ($T_{75}$) was seen at days 8-9. $T_{50}$ for CMC-treated (no rMuIL-12) irradiated female and male mice was days 11-12 and 12-13 respectively. Full wound closure was achieved for all rMuIL-12-treated mice by days 10-13. All treated groups show accelerated healing over time relative to control. Vehicle-treated irradiated female mice healed at a faster rate relative to vehicle-treated irradiated male mice. However, this sex-specific difference in healing was not observed in mice that received rMuIL-12.

Figure 4C:
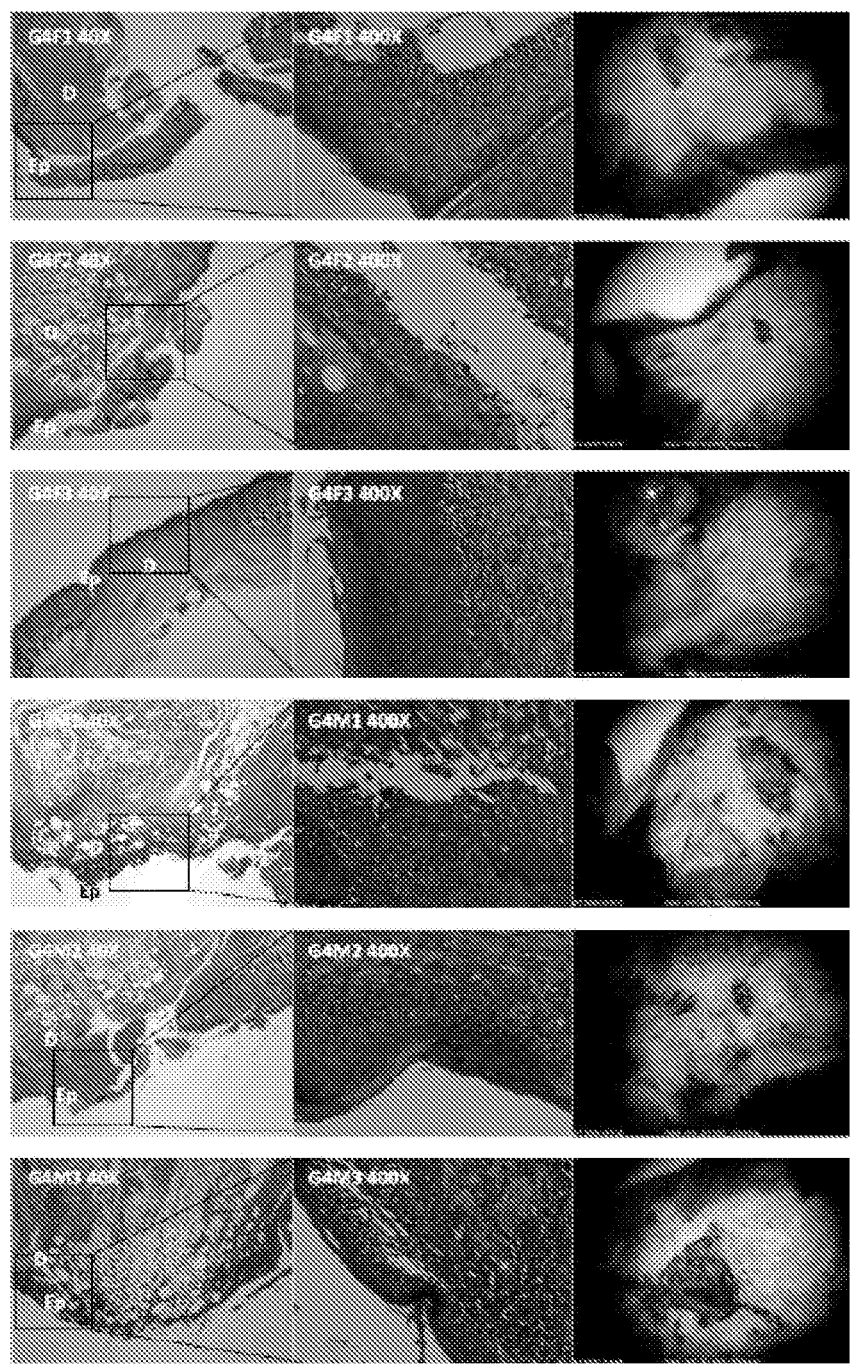
FIG. 4C shows a series of photomicrographs of trichrome-stained sections of skin wounds from mice treated with vehicle only, as well as the corresponding wound seen on the mouse itself (1×) (Ep=epidermis, D=dermis). Each row is a tissue section from a single animal, with the left photomicrograph taken at 40×, the middle photomicrograph taken at 400×, and the corresponding wound taken at 1× magnification.
Figure 4D:
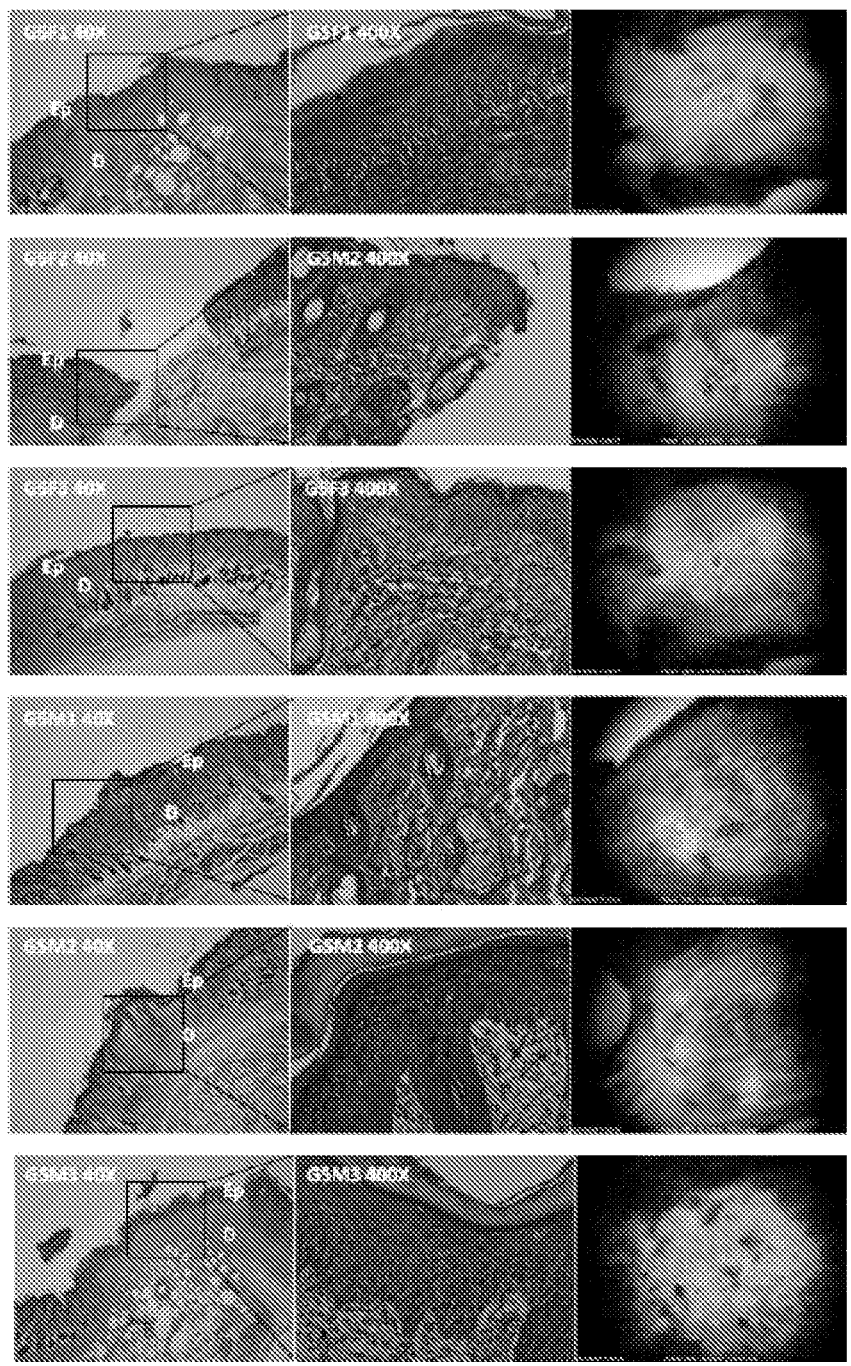
FIG. 4D shows photomicrographs from mice that received 100 ng/mL rMuIL-12.

At the 100 ng/mL rMuIL-12 dosage, the epidermal layer is composed of columnar, cuboidal, and squamous cells as well as a layer of keratinized epithelial tissue. In addition, many rMuIL-12-treated wounds showed the presence of advanced tertiary development as evidenced by the presence of sebaceous glands and hair follicles within the newly developed epidermis/dermis. FIG. 4C shows a series of photomicrographs of trichrome-stained sections of skin wounds from mice treated with vehicle only, as well as the corresponding wound seen on the mouse itself (1×) (Ep=epidermis, D=dermis). Each row is a tissue section from a single animal, with the left photomicrograph taken at 40×, the middle photomicrograph taken at 400×, and the corresponding wound taken at 1× magnification. Delayed and incomplete wound closure can be seen in these animals. FIG. 4D shows photomicrographs from mice that received 100 ng/mL rMuIL-12. These mice showed enhanced wound closure relative to controls.

Thus, rMuIL-12 accelerated wound healing in a radiation combined injury model. 100 ng/mL was sufficient to induce accelerated wound closure, and no increased rate of wound closure using 3160 ng/mL rMu-IL-12 was observed.

Example 4: Mitigation of Skin Wounds in Irradiated Mice Using IL-12 at 24 Hours Post-Injury A study was undertaken to examine the healing of full-thickness cutaneous injuries in irradiated mice, where rMuIL-12 is topically and/or subcutaneously administered to the wound 24 hours after the wound is created.
Materials and Methods Thirty mice received 500 cGy of total body irradiation in a Gammacell® 40 irradiator, and then given a 10.0 mm diameter wound using a biopsy punch, as described in Examples 2 and 3. The mice were then split into 5 treatment groups of 6 animals each Group 1 was treated with 4% CMC alone; Group 2 was treated with 4% CMC+100 ng/mL of rMuIL-12 immediately after receiving the wound; Group 3 was treated with 4% CMC+100 ng/mL of rMuIL-12 about 24 hours post-injury; Group 4 was treated with 4% CMC+ 100 ng/mL of rMuIL-12 and a subcutaneous injection of 20 ng/mL of rMuIL-12 about 24 hours post-injury; and Group 5 was treated with only a subcutaneous injection of 100 µl (20 ng) a 200 ng/mL solution of rMu-IL-12 about 24 hours post-injury.

Figure 5A:
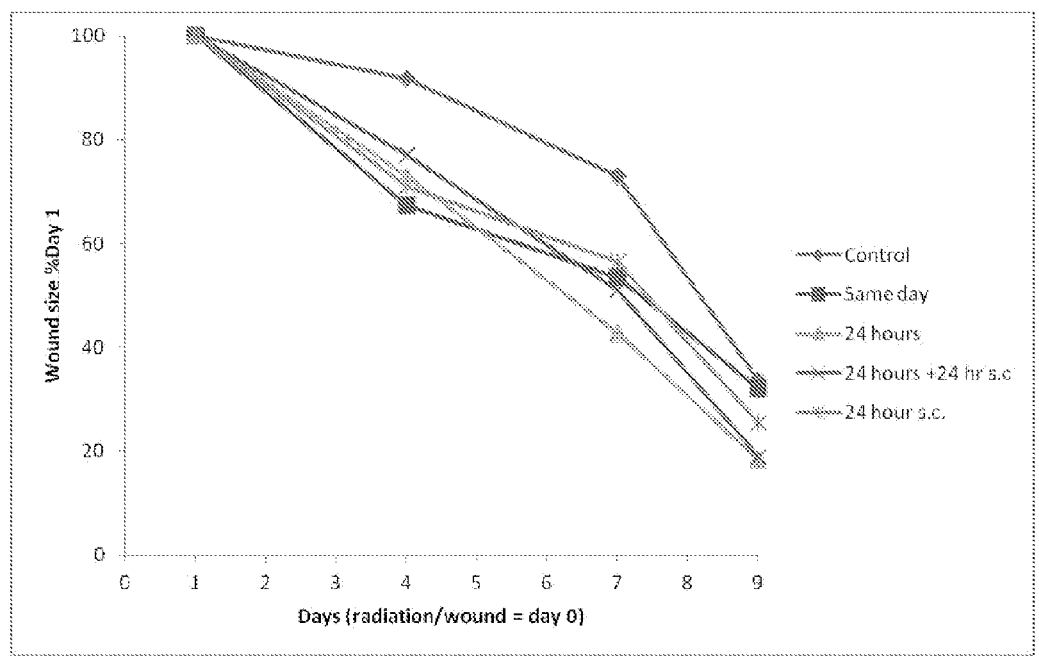
FIG. 5A is a graph of changes in the percentage of wound size over time (in days) for irradiated mice treated with rMuIL-12 topically and/or subcutaneously about 24 hours following creation of the wound.

Approximately 150 µl of CMC was delivered to each wound. This volume represents an approximate rMuIL-12 wound dosage of 15 ng (for 100 ng/mL concentration). Wound measurement is described in Example 1 (calculated area of wound=78.5 mm$^2$, mm diameter full-thickness wound, $\pi r^2$)
Results Topically-treated wounds from mice who received a combined radiation/full-thickness skin injury closed at a faster rate relative to vehicle-treated controls. FIG. 5A shows a graph of wound size as a percentage of that measured on Day 1 of the study (24 hours after the wounds were administered). FIG. 5B shows photographs of wounds at 1× for each of the treatment regimens. Co-administration of topical rMuIL-12 and a single subcutaneous injection of 20 ng rMuIL-12 afforded no significant boost in wound healing relative to animals receiving topical application of rMuIL-12. Animals who received a single subcutaneous administration of 20 ng rMuIL-12 at 24 hours post injury/irradiation healed at the same rate as topically-treated animals. Thus, rMuIL-12 administered even 24 hours following injury (topically and/or subcutaneously) results in increased rate of wound closure.

Example 5: Mitigation of Skin Wounds in Diabetic Rats Using IL-12

Figure 6A:
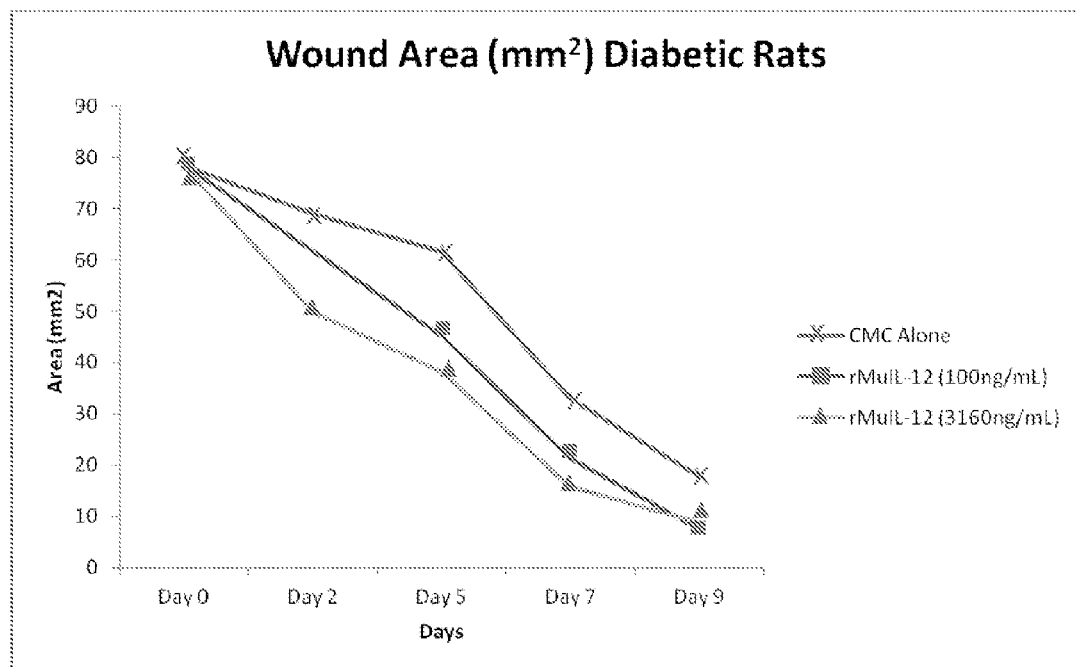
FIG. 6A shows a graph of wound area over days 0-9 for diabetic Zucker rats treated with vehicle only, 100 ng/mL of rMuIL-12, and 3160 ng/mL of rMuIL-12.
Figure 6B:
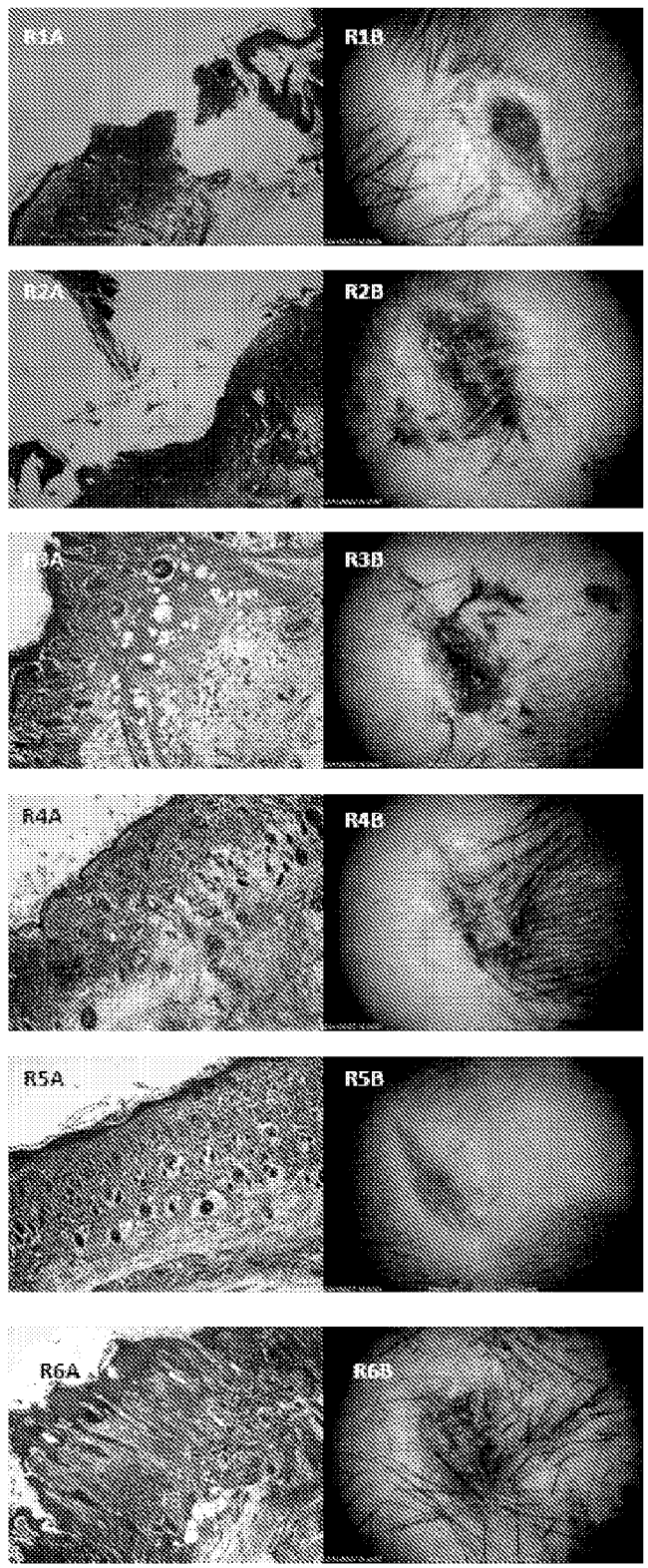
FIG. 6B shows trichrome-stained photomicrographs of mice treated with vehicle alone at day 9 of treatment (left side), along with corresponding 1× photographs of the wound (right side).
Figure 6C:
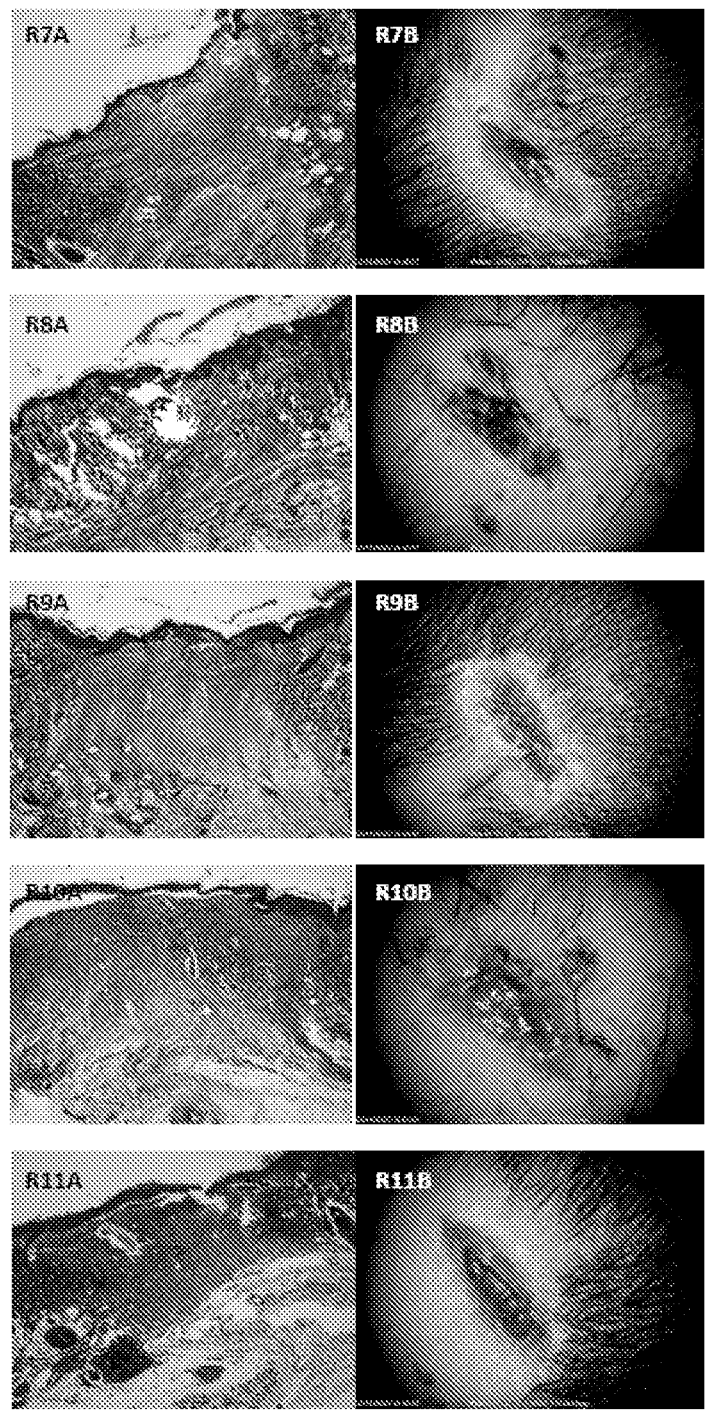
FIG. 6C shows trichrome-stained photomicrographs of mice treated with 100 ng/mL rMuIL-12 at day 9 of treatment (left side), along with corresponding 1× photographs of the wound (right side).

A study was undertaken to examine the healing of full-thickness cutaneous injuries in diabetic rats that were topically treated with vehicle alone or vehicle+rMuIL-12.
Materials and Methods Eighteen male Zucker rats were anesthetized and given a circular 10.0 mm diameter wound using a biopsy punch as described in Example 1. The rats were then divided into three treatment groups: Group 1 was treated with 4% CMC alone; Group 2 was treated with 4% CMC+100 ng/mL of rMuIL-12; and Group 3 was treated with 4% CMC+3160 ng/mL of rMuIL-12. Wounds were covered with Tegaderm as described in Example 1. Approximately 150 µl of CMC was delivered to each wound. This volume represents an approximate rMuIL-12 wound dosage of 15 ng (for 100 ng/mL concentration) or 474 ng (for 3160 ng/mL concentration). Wound measurements are as described in Example 1 (calculated area of wound=78.5 mm$^2$, 10 mm diameter full-thickness wound, $\pi r^2$)
Results Mice treated with rMuIL-12 healed faster relative to vehicle-treated controls. FIG. 6A shows a graph of wound area over days 0-9 for each of the treated groups. The wound response to rMuIL-12 seems to be somewhat dose-dependent. 50% wound closure ($T_{50}$) in rMuIL-12-treated (100 ng/mL) diabetic rats was observed at approximately day 6. $T_{50}$ in rMuIL-12-treated (3160 ng/mL) diabetic rats was observed at approximately day 5. $T_{50}$ for CMC-treated diabetic rats was observed at approximately day 7. Full wound closure was achieved for all rMuIL-12-treated mice by days 10-13. All treated groups show accelerated healing over time relative to control. FIG. 6B shows trichrome-stained photomicrographs of mice treated with vehicle alone at day 9 of treatment (left side), along with corresponding 1× photographs of the wound (right side). FIG. 6C shows trichrome-stained photomicrographs of mice treated with 100 ng/mL rMuIL-12 at day 9 of treatment (left side), along with corresponding 1× photographs of the wound (right side).

Thus, rMuIL-12 accelerated wound healing in a rat model of type II diabetes. A dosage of 100 ng/mL rMuIL-12 was sufficient to induce accelerated wound closure, and a dosage of 3160 ng/mL rMuIL-12 displayed an enhanced response relative to the 100 ng/mL group.

The above examples are given to illustrate the present invention. It should be understood, however, that the spirit and scope of the invention is not to be limited to the specific conditions or details described in these examples. All publicly available documents referenced herein, including but not limited to U.S. patents, are specifically incorporated by reference.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A method for treating a cutaneous wound in a subject, comprising subcutaneously administering a therapeutically effective amount of Interleukin-12 (IL-12) to a patient with a cutaneous wound, wherein the cutaneous wound is due to a burn, physical trauma, surgical trauma or an underlying factor slowing the wound closure.

2. The method of claim 1, wherein the subject is human.

3. The method of claim 1, further comprising a second administration of IL-12, wherein the second administration of IL-12 is administered subcutaneously or topically.

4. The method of claim 3, wherein the IL-12 is administered topically in a dosage of from about 1 ng/mL up to about 10 µg/mL.

5. The method of claim 3, wherein the IL-12 is administered topically in a dosage of from about 10 ng/mL up to about 5 µg/mL.

6. The method of claim 3, wherein the IL-12 is administered topically at a dosage of about 100 ng mL.

7. The method of claim 3, wherein the topically administered IL-12 is administered in conjunction with acellular or cellular dermal matrices.

8. The method of claim 3, wherein the topically administered IL-12 is emulsified in a gel matrix.

9. The method of claim 8, wherein the gel matrix is isotonic 4% carboxymethylcellulose.

10. The method of claim 1, wherein the IL-12 is administered subcutaneously in a dosage of from about 10 ng/kg to about 500 ng/kg.

11. The method of claim 10, wherein the IL-12 is administered subcutaneously in a dosage of about 100-200 ng/kg.

12. The method of claim 1, wherein the wound is an open wound.

13. The method of claim 12, wherein administration of IL-12 results in at least about a 5% increase in wound healing as measured by wound closure over a specified time period, as compared to wound closure observed in the absence of IL-12 administration.

14. The method of claim 12, wherein administration of IL-12 results in at least about a 20% increase in wound healing as measured by wound closure over a specified time period, as compared to wound closure observed in the absence of IL-12 administration.

15. The method of claim 12 wherein administration of IL-12 results in at least about a 50% increase in wound healing as measured by wound closure over a specified time period, as compared to wound closure observed in the absence of IL-12 administration.

16. The method of claim 12, wherein administration of IL-12 results in at least about a 75% increase in wound healing as measured by wound closure over a specified time period, as compared to wound closure observed in the absence of IL-12 administration.

17. The method of claim 12, wherein administration of IL-12 results in at least about a 95% increase in wound healing as measured by wound closure over a specified time period, as compared to wound closure observed in the absence of IL-12 administration.

18. The method of claim 1, wherein the burn was caused by exposure to radiation, which results in a cutaneous wound.

19. The method of claim 18, wherein the IL-12 is administered from about 1 hour up to about 120 hours following exposure to radiation resulting in a cutaneous wound.

20. The method of claim 18, wherein the radiation is gamma radiation.

21. The method of claim 1, wherein the subject is a member of a patient population characterized by an impediment to normal cutaneous wound healing.

22. The method of claim 1, wherein the subject is diabetic.

23. The method of claim 1, wherein the burn is a second, third or fourth degree burn.

24. The method of claim 1, wherein the surgical trauma is present at a surgical site.

25. The method of claim 24, wherein administration of IL-12 results in a decrease in the incidence of infection at the surgical site.

26. The method of claim 1, wherein the IL-12 is administered in conjunction with a skin graft.

27. The method of claim 1, wherein the wound is a full-thickness wound or a partial thickness wound.

28. The method of claim 1, wherein the subject is elderly.

29. The method of claim 28, wherein administration of IL-12 results in a decrease in the incidence of infection of a diabetic ulcer.

* * * * *